United States Patent
Grue-Sørensen et al.

(10) Patent No.: US 7,071,178 B2
(45) Date of Patent: Jul. 4, 2006

(54) USE OF VITAMIN D-DERIVATIVES IN THE TREATMENT OF OSTEOPOROSIS AND RELATED BONE DISORDERS, AS WELL AS NOVEL VITAMIN D3-DERIVATIVES

(75) Inventors: Gunnar Grue-Sørensen, Roskilde (DK); Henrik Pedersen, Roskilde (DK); Ernst Torndal Binderup, Taastrup (DK); Mikael Tranholm, Frederiksberg (DK)

(73) Assignee: Leo Pharmaceutical Products, Ltd., Ballerup (DK)

( * ) Notice: Subject to any disclaimer, the term of this patent is extended or adjusted under 35 U.S.C. 154(b) by 230 days.

(21) Appl. No.: 09/787,548

(22) PCT Filed: Jan. 31, 2001

(86) PCT No.: PCT/DK01/00069

§ 371 (c)(1),
(2), (4) Date: May 29, 2001

(87) PCT Pub. No.: WO01/56981

PCT Pub. Date: Aug. 9, 2001

(65) Prior Publication Data

US 2004/0069523 A1    Apr. 15, 2004

Related U.S. Application Data

(60) Provisional application No. 60/179,426, filed on Jan. 31, 2000.

(51) Int. Cl.
*A61K 31/59*    (2006.01)
(52) U.S. Cl. .................................................. 514/167
(58) Field of Classification Search ................ 552/653; 514/167
See application file for complete search history.

(56) References Cited

U.S. PATENT DOCUMENTS

| | | | | |
|---|---|---|---|---|
| 3,163,836 A | * | 12/1964 | Sugi et al. .................. | 174/108 |
| 3,588,317 A | * | 6/1971 | Hutchins, Jr. ........... | 174/106 R |
| 4,849,288 A | * | 7/1989 | Schmaderer et al. | |
| 5,374,629 A | * | 12/1994 | Calverley et al. ........... | 514/167 |
| 5,929,385 A | * | 7/1999 | Sugimoto et al. ........ | 174/125.1 |
| 5,952,614 A | * | 9/1999 | Ries ....................... | 174/106 R |

FOREIGN PATENT DOCUMENTS

| | | | |
|---|---|---|---|
| EP | 0 567 353 A1 | | 10/1993 |
| WO | WO 91/15475 | * | 10/1991 |
| WO | WO 96/39705 | * | 12/1996 |

OTHER PUBLICATIONS

D'Armour, "The role of parathyroid hormone and hyperparathyroidism in osteoporosis." Osteoporosis Primer, 2000, 211-224. Abstract attached.*

Fukunaga, "Characteristics of bone mass change in secondary osteoporosis." Clinical Calcium, 1994, vol. 4(8), 1099-1101. Abstract attached.*

Kurabayashi, "Developmental mechanism and management of osteoporosis induced by endocrine disorder." Rinsho to Yakubutsu Chiryo, 1995, vol. 14(6), 521-524. Abstract attached.*

* cited by examiner

*Primary Examiner*—Barbara P. Badio
(74) *Attorney, Agent, or Firm*—Birch, Stewart, Kolasch & Birch, LLP

(57) ABSTRACT

Compounds of the formula I

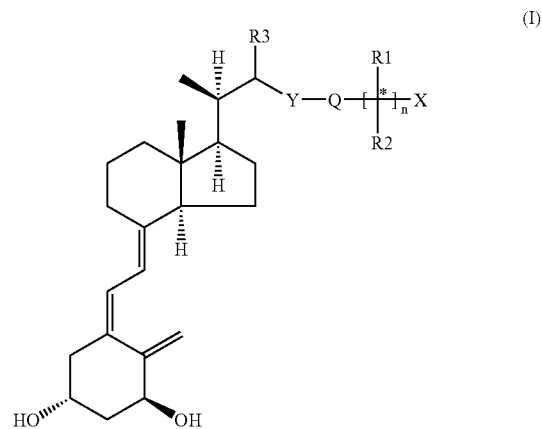

wherein
X represents hydrogen or hydroxy;
Y represents oxygen or sulphur or oxidized sulphur selected from the groups S(O) and S($O_2$);
$R^1$ and $R^2$, which may be the same or different, represent hydrogen or a residue after removal of 1 hydrogen atom from a straight, branched or cyclic, saturated or unsaturated, $C_1$–$C_6$-hydrocarbon; or $R^1$ and $R^2$, together with the carbon atom to which they are attached (marked with an asterisk in formula I), bearing the group X, form a $C_3$–$C_8$ carbocyclic ring;
Q represents a diradical residue after removal of 2 hydrogen atoms from a straight, branched or cyclic, saturated or unsaturated $C_1$–$C_8$-hydrocarbon; and
$R^3$ represents hydrogen or a residue after removal of 1 hydrogen atom from a straight, branched or cyclic, saturated or unsaturated $C_1$–$C_6$-hydrocarbon;
may be used for the preparation of a medicament for the treatment and/or prophylaxis of osteoporosis and related bone disorders.

19 Claims, 2 Drawing Sheets

USE OF VITAMIN D-DERIVATIVES IN THE TREATMENT OF OSTEOPOROSIS AND RELATED BONE DISORDERS, AS WELL AS NOVEL VITAMIN D3-DERIVATIVES

This application is the national phase of international application PCT/DK01/00069 filed Jan. 31, 2001 which designated the U.S.

This application also claims the benefit of U.S. Provisional Application No. 60/179,426, filed Jan. 31, 2000.

FIELD OF THE INVENTION

The present invention relates to the use of pharmacologically active vitamin D analogues in a novel medical prophylaxis and treatment of osteoporosis and related bone disorders as well as pharmaceutical preparations containing these compounds and dosage units of such preparations. The present invention further relates to novel pharmacologically active vitamin D analogues as well as pharmaceutical preparations containing these compounds and dosage units of such preparations.

BACKGROUND OF THE INVENTION

It has recently been shown that $1\alpha,25$-dihydroxyvitamin $D_3$ ($1,25(OH)_2D_3$) has an effect in relation to bone anabolism indicating the potential use of this compound in the treatment of osteoporosis and conditions characterized by an abnormal bone mineralisation. Erben et al. (Endocrinology, 139, 4319–4328 (1998)) have provided evidence for a direct anabolic effect of $1,25(OH)_2D_3$ on bone.

However, the therapeutic possibilities of $1,25(OH)_2D_3$ in such indications are severely limited by the well known potent effect of this hormone on calcium metabolism; elevated blood concentrations will rapidly give rise to hypercalcemia. Thus, this compound is not completely satisfactory for use as a drug in the treatment of osteoporosis which may require prolonged administration of the drug in relatively high doses.

A number of oxa- and thia-analogues of vitamin $D_3$ are known. $1\alpha,25$-dihydroxy-20-oxa-21-norvitamin $D_3$ and $1\alpha$-hydroxy-20-oxa-21-norvitamin $D_3$ are described in N. Kubodera et al., Chem. Pharm. Bull., 34, 2286 (1986), $1\alpha,25$-dihydroxy-22-oxavitamin $D_3$ and 25-hydroxy-22-oxavitamin $D_3$ are described in E. Murayama et al., Chem. Pharm. Bull., 34, 4410 (1986), J. Abe et al., FEBS LETTERS, 226, 58 (1987) and European Patent Application, publication number 184 112, and $1\alpha,25$-dihydroxy-23-oxavitamin $D_3$ and $1\alpha,25$-dihydroxy-23-thiavitamin $D_3$ are described in European Patent Application publication number 78704. 24- and 25-sulphonyl-analogues of $1\alpha,25$-dihydroxy-vitamin $D_3$ have been described in G. H. Posner et al., J. Med. Chem., 42, 3425 (1999).

Some of these compounds may have advantages over $1,25(OH)_2D_3$ in having reduced calcium metabolism effects relative to $1,25(OH)_2D_3$. However, there is no report on a possible effect of these compounds in relation to bone anabolism.

SUMMARY OF THE INVENTION

Because of the serious medical implications for the affected individual, and the relatively limited numbers of drugs available for treatment of osteoporosis and the severity of the known side effects of $1,25(OH)_2D_3$, the object of the present invention is to provide active vitamin D analogues including novel analogues for the preparation of medicaments for adequate therapy of osteoporosis including the use of said compounds for the preparation of medicaments for promoting osteogenesis and treating or preventing osteoporosis, such as steroid induced, senile and post menopausal osteoporosis; osteomalacia and related bone disorders. It is a further object of the invention to provide active vitamin D analogues including novel analogues for the preparation of medicaments for improving muscle strength including treatment of skeletal muscle weakness.

The present inventors have surprisingly found that previously disclosed vitamin D analogues reported to possess antiinflammatory and immunomodulating effects as well as inhibiting proliferation of certain cells, said analogues being represented by general formula I herein, and novel compounds of general formula I have shown bone anabolic effects in an in vivo model of osteoporosis and related bone disorders. Moreover, the bone anabolic activity of the analogues of the invention including the novel compounds is accompanied by a strengthening effect on the skeletal muscles. Thus rendering the present compounds even more useful in various medical treatments, especially relating to treatment of osteoporosis.

Thus, the object of the present invention is achieved with the selected vitamin D analogues having the general formulae I and Ia below. The general formula I of the present active compounds has previously been disclosed in international patent application No. WO 91/15475 which is hereby incorporated by reference in its entirety and which discloses the use of these compounds for the treatment of hyperparathyroidism among other disease states.

Accordingly, the present invention relates to the use of compounds represented by the general formula I

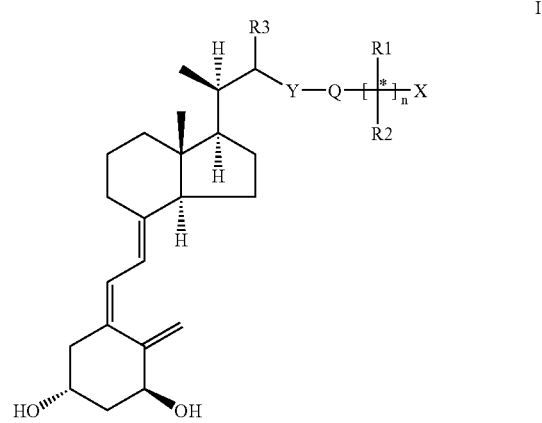

I wherein

X represents hydrogen or hydroxy;

Y represents oxygen or sulphur or oxidized sulphur selected from the groups S(O) and S(O$_2$);

$R^1$ and $R^2$, which may be the same or different, represent hydrogen or a residue after removal of 1 hydrogen atom from a straight, branched or cyclic, saturated or unsaturated, $C_1$–$C_6$-hydrocarbon; or $R^1$ and $R^2$, together with the carbon atom to which they are attached (marked with an asterisk in formula I), bearing the group X, form a $C_3$–$C_8$ carbocyclic ring;

Q represents a diradical residue after removal of 2 hydrogen atoms from a straight, branched or cyclic, saturated or unsaturated $C_1$–$C_8$-hydrocarbon;

R³ represents hydrogen or a residue after removal of 1 hydrogen atom from a straight, branched or cyclic, saturated or unsaturated $C_1$–$C_6$-hydrocarbon;

R¹, R² and/or Q is optionally substituted with one or more deuterium or fluorine atoms; and n is 0 or 1;

and derivatives of the compounds of formula I in which one or more hydroxy groups have been transformed into —O-acyl or —O-glycosyl groups, or a phosphate ester, such masked groups being hydrolyzable in vivo; for the preparation of a medicament for the treatment and/or prophylaxis of osteoporosis and related bone disorders.

DETAILED DESCRIPTION OF THE INVENTION

In the use according to the present invention preferred compounds of formula I are compounds wherein Y represents sulphur or oxidized sulphur, such as S(O) or S(O$_2$); and/or compounds of formula I wherein R¹ and R², together with the carbon atom to which they are attached, bearing the group X, form a $C_3$–$C_5$ olefinic group, such as a $C_3$–$C_5$ alkenyl group, or a $C_3$–$C_5$ carbocyclic ring, said ring preferably being saturated, such as $C_3$–$C_5$ alkylene; and/or compounds of formula I wherein X represents hydroxy; and/or compounds of formula I wherein Q represents a phenylene group optionally substituted with one or more fluorine atoms; and/or compounds of formula I wherein R³ represents hydrogen; and/or compounds of formula I wherein n is 1.

Examples of specific compounds useful in the invention are:

1(S),3(R)-Dihydroxy-20(R)-(2-hydroxy-2-methyl-1-propoxymethyl)-9,10-seco-pregna-5(Z),7(E),10(19)-triene (Compound 101), 1(S),3(R)-Dihydroxy-20(R)-(4-hydroxy-1-butoxymethyl)-9,10-seco-pregna-5(Z),7(E),10(19)-triene (Compound 104), 1(S),3(R)-Dihydroxy-20(R)-(4-hydroxy-4-methyl-1-pentyloxymethyl)-9,10-seco-pregna-5(Z),7(E),10(19)-triene (Compound 105), 1(S),3(R)-Dihydroxy-20(R)-[3-(1-hydroxy-cyclohex-1-yl)-prop-2-yn-1-yloxymethyl]-9,10-seco-pregna-5(Z),7(E),10(19)-triene (Compound 110), 1(S),3(R)-Dihydroxy-20(R)-22(S)-methyl-(4-hydroxy-pent-2E-en-1-yloxymethyl)-9,10-seco-pregna-5(Z),7(E),10(19)-triene (Compound 112), 1(S),3(R)-Dihydroxy-20(R)-22(R)-methyl-(4-hydroxy-pent-2E-en-1-yloxymethyl)-9,10-seco-pregna-5(Z),7(E),10(19)-triene (Compound 113), 1(S),3(R)-Dihydroxy-20(R)-(2-cyclopropyl-2(S)-hydroxy-ethyl)-thiomethyl]-9,10-seco-pregna-5(Z),7(E),10(19)-triene (Compound 114), 1(S),3(R)-Dihydroxy-20(R)-(2-cyclopropyl-2(R)-hydroxy-ethyl)-thiomethyl]-9,10-seco-pregna-5(Z),7(E),10(19)-triene (Compound 115), 1(S),3(R)-Dihydroxy-20(R)-(3-hydroxy-3-methyl-1-butyl-sulphinylmethyl)-9,10-seco-pregna-5(Z),7(E),10(19)-triene (Compound 118 and 119), 1(S),3(R)-Dihydroxy-20(R)-(3-hydroxy-3-methyl-1-butyl-sulphonylmethyl)-9,10-seco-pregna-5(Z),7(E),10(19)-triene (Compound 120), 1(S),3(R)-Dihydroxy-20(R)-22(S)-methyl-(3-hydroxy-3-methyl-1-butylthiomethyl)-9,10-seco-pregna-5(Z),7(E),10(19)-triene (Compound 122), 1(S),3(R)-Dihydroxy-20(R)-22(R)-methyl-(3-hydroxy-3-methyl-1-butylthiomethyl)-9,10-seco-pregna-5(Z),7(E),10(19)-triene (Compound 123), 1(S),3(R)-Dihydroxy-20(R)-22(S)-methyl-(3-hydroxy-3-ethyl-1-pentylthiomethyl)-9,10-seco-pregna-5(Z),7(E),10(19)-triene (Compound 124), 1(S),3(R)-Dihydroxy-20(R)-22(R)-methyl-(3-hydroxy-3-ethyl-1-pentylthiomethyl)-9,10-seco-pregna-5(Z),7(E),10(19)-triene (Compound 125), 1(S),3(R)-Dihydroxy-20(R)-(2-((1-hydroxy-1-ethyl)propyl)phenylthiomethyl)-9,10-seco-pregna-5(Z),7(E),10(19)-triene (Compound 143), 1(S),3(R)-Dihydroxy-20(R)-(4-((1-hydroxy-1-ethyl)propyl)phenylthiomethyl)-9,10-seco-pregna-5(Z),7(E),10(19)-triene (Compound 146), 1(S),3(R)-Dihydroxy-20(R)-(3-hydroxy-phenylthiomethyl)-9,10-seco-pregna-5(Z),7(E),10(19)-triene (Compound 148), 1(S),3(R)-Dihydroxy-20(R)-(2-hydroxy-2-ethyl-1-butylthiomethyl)-9,10-seco-pregna-5(Z),7(E),10(19)-triene (Compound 150), 1(S),3(R)-Dihydroxy-20(R)-(4-hydroxy-4-ethyl-1-hexylthiomethyl)-9,10-seco-pregna-5(Z),7(E),10(19)-triene (Compound 151), 1(S),3(R)-Dihydroxy-20(R)-(3-hydroxy-phenoxymethyl)-9,10-seco-pregna-5(Z),7(E),10(19)-triene (Compound 152), and 1(S),3(R)-Dihydroxy-20(R)-(4-hydroxy-4-methyl-1-pent-2(Z)-enyloxymethyl-9,10-seco-pregna-5(Z),7(E),10(19)-triene (Compound 154).

Preferred compounds useful in the invention are:

1(S),3(R)-Dihydroxy-20(R)-(3-hydroxy-3-methyl-1-butoxymethyl)-9,10-seco-pregna-5(Z),7(E),10(19)-triene (Compound 102), 1(S),3(R)-Dihydroxy-20(R)-(3-hydroxy-3-ethyl-1-pentyloxymethyl-9,10-seco-pregna-5(Z),7(E),10(19)-triene (Compound 103), 1(S),3(R)-Dihydroxy-20(R)-(4-hydroxy-4-methyl-1-pentyloxymethyl)-9,10-seco-pregna-(Z),7(E),10(19)-triene (Compound 106), 1(S),3(R)-Dihydroxy-20(R)-(4-hydroxy-4-methyl-1-pent-2 (E)-enyloxymethyl)-9,10-seco-pregna-5(Z),7(E),10(19)-triene (Compound 107), 1(S),3(R)-Dihydroxy-20(R)-(4-hydroxy-4-methyl-1-pent-2-ynyloxymethyl)-9,10-seco-pregna-5(Z),7(E),10(19)-triene (Compound 108), 1(S),3(R)-Dihydroxy-20(R)-(4-hydroxy-4-trifluoromethyl-5,5,5-trifluoro-1-pent-2-ynyloxymethyl)-9,10-seco-pregna-5(Z),7(E),10(19)-triene (Compound 109), 1(S),3(R)-Dihydroxy-20(R)-[3-(2-hydroxy-2-propyl)-phenoxymethyl]-9,10-seco-pregna-5(Z),7(E),10(19)-triene (Compound 111), 1(S),3(R)-Dihydroxy-20(R)-(2-hydroxy-2-methyl-1-propylthiomethyl)-9,10-seco-pregna-5(Z),7(E),10(19)-triene (Compound 116), 1(S),3(R)-Dihydroxy-20(R)-(3-hydroxy-3-methyl-1-butylthiomethyl)-9,10-seco-pregna-5(Z),7(E),10(19)-triene (Compound 117), 1(S),3(R)-Dihydroxy-20(R)-(3-hydroxy-3-ethyl-1-pentylthiomethyl)-9,10-seco-pregna-5(Z),7(E),10(19)-triene (Compound 121), 1(S),3(R)-Dihydroxy-20(R)-(5-hydroxy-5-methyl-1-hexyloxymethyl)-9,10-seco-pregna-5(Z),7(E),10(19)-triene (Compound 126), 1(S),3(R)-Dihydroxy-20(R)-[2-(2-hydroxy-2-propyl)-phenoxymethyl]-9,10-seco-pregna-5(Z),7(E),10(19)-triene (Compound 127), 1(S),3(R)-Dihydroxy-20(R)-[2-(3-hydroxy-3-pentyl)-phenoxymethyl]-9,10-seco-pregna-5(Z),7(E),10(19)-triene (Compound 128), 1(S),3(R)-Dihydroxy-20(R)-[3-(3-hydroxy-3-pentyl)-phenoxymethyl]-9,10-seco-pregna-5(Z),7(E),10(19)-triene (Compound 129), 1(S),3(R)-Dihydroxy-20(R)-[4-(2-hydroxy-2-propyl)-phe-noxymethyl]-9,10-seco-pregna-5(Z),7(E),10(19)-triene (Compound 130), 1(S),3(R)-Dihydroxy-20(R)-[4-(3-hydroxy-3-pentyl)-phe-noxymethyl]-9,10-seco-pregna-5(Z),7(E),10(19)-triene (Compound 131), 1(S),3(R)-Dihydroxy-20(R)-[3-(hydroxymethyl)-phe-noxymethyl]-9,10-seco-pregna-5(Z),7(E),10(19)-triene (Compound 132), 1(S),3(R)-Dihydroxy-20(R)-(3-hydroxy-3-ethyl-1-pentyl-sulphinylmethyl-9,10-seco-pregna-5(Z),7(E),10(19)-triene (Compound 133), 1(S),3(R)-Dihydroxy-20(R)-(3-hydroxy-3-ethyl-1-pentyl-sulphinylmethyl)-9,10-seco-pregna-5(Z),7(E),10(19)-triene (Compound 134), 1(S),3(R)-Dihydroxy-20(R)-(3-hydroxy-3-ethyl-1-pentyl-sulphonylmethyl)-9,10-seco-pregna-5(Z),7(E),-10(19)-triene (Compound 135), 1(S),3(R)-Dihydroxy-20(R)-(4-hydroxy-4-methyl-1-pen-tylthiomethyl)-9,10-seco-pregna-5(Z),7(E),10(19)-triene (Compound 136), 1(S),3(R)-Dihydroxy-20(R)-(3-(hydroxymethyl)phenylthi-omethyl)-9,10-seco-pregna-5(Z),7(E),10(19)-triene (Compound 137), 1(S),3(R)-Dihydroxy-20(R)-(3-((1-hydroxy-1-methyl)ethyl)phenylthiomethyl)-9,10-seco-pregna-5(Z),7(E),-10(19)-triene (Compound 138), 1(S),3(R)-Dihydroxy-20(R)-(4-hydroxy-4-ethyl-1-hex-2-ynyloxymethyl)-9,10-seco-pregna-5(Z),7(E),10(19)-triene (Compound 139), 1(S),3(R)-Dihydroxy-20(R)-(2-hydroxyphenoxymethyl)-9,10-seco-pregna-5(Z),7(E),10(19)-triene (Compound 140), 1(S),3(R)-Dihydroxy-20(R)-(3-hydroxyphenoxymethyl)-9,10-seco-pregna-5(Z),7(E),10(19)-triene (Compound 141), 1(S),3(R)-Dihydroxy-20(R)-(2-((1-hydroxy-1-methyl)ethyl)phenylthiomethyl)-9,10-seco-pregna-5(Z),7(E),10(19)-triene (Compound 142), 1(S),3(R)-Dihydroxy-20(R)-(3-((1-hydroxy-1-ethyl)propyl)phenylthiomethyl)-9,10-seco-pregna-5(Z),7(E),10(19)-triene (Compound 144), 1(S),3(R)-Dihydroxy-20(R)-(4-((1-hydroxy-1-methyl)ethyl)phenylthiomethyl)-9,10-seco-pregna-5(Z),7(E),10(19)-triene (Compound 145), 1(S),3(R)-Dihydroxy-20(R)-(2-hydroxy)phenylthiom-ethyl)-9,10-seco-pregna-5(Z),7(E),10(19)-triene (Compound 147), 1(S),3(R)-Dihydroxy-20(R)-(4-hydroxy-phenylthiom-ethyl)-9,10-seco-pregna-5(Z),7(E),10(19)-triene (Compound 149), 1(S),3(R)-Dihydroxy-20(R)-(3,3-difluoro-4-hydroxy-4-me-thyl-1-pentyloxymethyl)-9,10-seco-pregna-5(Z),-7(E),10(19)-triene (Compound 153), 1(S),3(R)-Dihydroxy-20(R)-(4-(hydroxymethyl)phenylthi-omethyl)-9,10-seco-pregna-5(Z),7(E),10(19)-triene (Compound 163), 1(S),3(R)-Dihydroxy-20(R)-(4-((1-hydroxy-1-ethyl)pro-pyl))phenylthiomethyl)-9,10-seco-pregna-5(Z),7(E),10(19)-triene (Compound 164), 1(S),3(R)-Dihydroxy-20(R)-(4-((1-hydroxy-1-methyl)ethyl))phenylthiomethyl)-22(R)-methyl-9,10-seco-pre-gna-5(Z),7(E),10(19)-triene (Compound 165), 1(S),3(R)-Dihydroxy-20(R)-(4-((1-hydroxy-1-methyl)ethyl))phenylthiomethyl)-22(S)-methyl-9,10-seco-pre-gna-5(Z),7(E),10(19)-triene (Compound 166), and derivatives of said compounds wherein one or more hydroxy groups have been transformed into —O-acyl or —O-glycosyl groups, or a phosphate ester, such masked groups being hydrolyzable in vivo, for the preparation of a medicament for the treatment and/or prophylaxis of osteoporosis and related bone disorders.

Examples of $R^1$ and $R^2$ when taken separately include (apart from hydrogen) methyl, trifluoromethyl, ethyl, vinyl, normal-, iso- and cyclo-propyl, and 1-methylvinyl. When $R^1$ and $R^2$ are different, it is preferred that $R^1$ represents hydrogen and $R^2$ represents cyclopropyl. Preferred are compounds wherein $R^1 = R^2$ represents methyl, ethyl, hydrogen or $CF_3$.

It is preferred to use compounds of general formula I wherein $R^1$ and $R^2$ each independently represents a $C_1$–$C_2$-alkyl group such as methyl and ethyl, and wherein Q represents a 1,4-substituted phenylene.

Examples of $R^1$ and $R^2$ when taken together include di-, tri-, tetra- and penta-methylene. Preferred is penta-methylene.

Examples of Q include methylene, di-, tri- and tetra-methylene, —$CH_2$—$CH=CH$—, —$CH_2$—$C\equiv C$—, $(CH_2)_2CF_2$, phenylene ($C_6H_4$; ortho, meta, para), —$CH_2$—($C_6H_4$)- (ortho, meta, para), and —($C_6H_4$)—$CH_2$ (ortho, meta, para). Preferred are $C_6H_4$ meta and para. $C_6H_4$ para being most preferred.

Examples of $R^3$ include (apart from hydrogen) methyl, normal-butyl and phenyl. Preferred are hydrogen and methyl.

Derivatives of formula I in which one or more of the hydroxy groups are masked as groups which can be reconverted to hydroxy groups in vivo are also within the scope of the invention ("bioreversible derivatives or prodrugs of I"). The term "bioreversible derivatives or prodrugs of I" includes, but is not limited to, derivatives of the compounds of said formula in which one or more hydroxy groups have been transformed into —O-acyl or —O-glycosyl groups, or a phosphate ester, such masked groups being hydrolyzable in vivo. The compounds I in which X is hydrogen are another type of prodrug. These compounds are relatively inactive in vitro, but may be converted to active compounds of formula I by enzymatic hydroxylation after administration to the patient.

Furthermore, the present invention relates to compounds of formula Ia

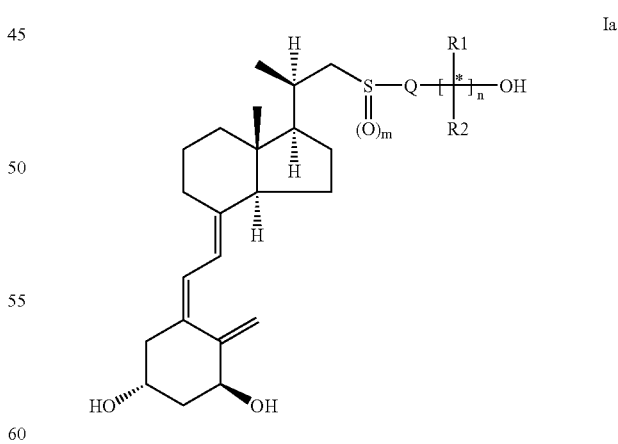

wherein $R^1$, $R^2$, and Q have the meanings specified above, m=0, 1 or 2; and n=1. Preferred are compounds of formula Ia wherein $R^1$ and $R^2$ when taken separately include (apart from hydrogen) methyl, trifluoromethyl, ethyl, vinyl, normal-, iso- and cyclo-propyl, and 1-methylvinyl. More preferred are also compounds of formula Ia wherein $R^1 = R^2$ or wherein $R^1$ and $R^2$ each independently represents a $C_1$–$C_2$-alkyl group such as methyl and ethyl, methyl being preferred.

Preferred are compounds of formula Ia wherein Q include methylene, di-, tri- and tetra-methylene, —CH$_2$—CH═CH—, —CH$_2$—C≡C—, phenylene (C$_6$H$_4$; ortho, meta, para), —CH$_2$—(C$_6$H$_4$)-(ortho, meta, para), and —(C$_6$H$_4$)—CH$_2$ (ortho, meta, para). More preferred are compounds of formula Ia wherein Q represents a straight chain propylene which is preferably substituted with one or two fluorine atoms, or wherein Q represents an unsubstituted phenylene group. It is preferred that Q represents CH$_2$CH$_2$CF$_2$, meta-C$_6$H$_4$ or para-C$_6$H$_4$.

The compounds of formula Ia are also preferably selected from the group consisting of:

1(S),3(R)-Dihydroxy-20(R)-(3,3-difluoro-4-hydroxy-4-methyl-1-pentylthiomethyl)-9,10-seco-pregna-5(Z),7(E),10(19)-triene (Compound 155), 1(S),3(R)-Dihydroxy-20(R)-(3,3-difluoro-4-hydroxy-4-methyl-1-pentylsulphinylmethyl)-9,10-seco-pregna-5(Z),7(E),10(19)-triene (Compound 156), 1(S),3(R)-Dihydroxy-20(R)-(3-((1-hydroxy-1-methyl)ethyl)phenylsulphinylmethyl)-9,10-seco-pregna-5(Z),7(E),10(19)-triene (isomer with Compound 159) (Compound 157), 1(S),3(R)-Dihydroxy-20(R)-(3-((1-hydroxy-1-methyl)ethyl)phenylsulphonylmethyl)-9,10-seco-pregna-5(Z),7(E),10(19)-triene (Compound 158), 1(S),3(R)-Dihydroxy-20(R)-(3-((1-hydroxy-1-methyl)ethyl)phenylsulphinylmethyl)-9,10-seco-pregna-5(Z),7(E),10(19)-triene (isomer with Compound 157) (Compound 159), 1(S),3(R)-Dihydroxy-20(R)-(4-((1-hydroxy-1-methyl)ethyl)phenylsulphonylmethyl)-9,10-seco-pregna-5(Z),7(E),10(19)-triene (Compound 160), 1(S),3(R)-Dihydroxy-20(R)-(4-((1-hydroxy-1-methyl)ethyl)phenylsulphinylmethyl)-9,10-seco-pregna-5(Z),7(E),10(19)-triene (isomer with Compound 162) (Compound 161), and 1(S),3(R)-Dihydroxy-20(R)-(4-((1-hydroxy-1-methyl)ethyl)phenylsulphinylmethyl)-9,10-seco-pregna-5(Z),7(E),10(19)-triene (isomer with Compound 161) (Compound 162).

Definitions

"$C_3$–$C_8$ carbocyclic ring" includes the saturated cycloalkanes and unsaturated cyclic olefins, such as cycloalkenes having one endocyclic double bond, and having from 3–8 carbon atoms.

Where the terms "comprise", "comprises", "comprised" or "comprising" are used in this specification, they are to be interpreted as specifying the presence of the stated features, integers, steps or components referred to, but not to preclude the presence or addition of one or more other feature, integer, step, component or group thereof.

As can be seen from formulae I and Ia, depending on the meanings of $R^1$, $R^2$, $R^3$ and X the compounds of the invention can comprise several diastereoisomeric forms (e.g. R or S configuration at the carbon atom marked with an asterisk). The invention covers all these diastereoisomers in pure form and also mixtures of diastereoisomers. The compounds of the present invention differ structurally from all the above mentioned oxa and thia compounds in that they possess R-configuration at the 20-position.

The compounds of formula I or Ia in which Y═O or S may conveniently be prepared from the vitamin D-derivative 1 (Tetrahedron, 43, 4609 (1987)) for example by the routes outlined in Scheme 1 and 2. O-Alkylation of Ib or S-alkylation of III to give IV is achieved by treatment under basic conditions with a side chain building block of general formula Z-R, in which Z is a leaving group such as a halogen (Cl, Br or I) or p-toluenesulphonyloxy or trifluoromethane-sulphonyloxy, and R is -(Q)-[C(R$^1$)(R$^2$)]$_n$X or optionally a radical which can be converted to this at any convenient later stage (or over several stages). Thus R in compounds IV, V, VI and VII does not necessarily have the same meaning along a particular synthetic sequence. The conversion of R to -(Q)-[C(R$^1$)(R$^2$)]$_n$X may well involve several steps and possibly involve a temporary protection of the sensitive triene system of the molecule. An alternative to this route involves treatment of the intermediate II (Z is a leaving group as described above) under basic conditions with a side chain building block HY—R, in which Y is oxygen or sulphur and R is as described above, to give the intermediate IV. Apart from any necessary modification within the side chain (R), the conversion of IV to I involves a photoisomerisation step and a desilylation step, analogous to the steps used in the last stages of the synthesis of other vitamin D analogues (see European patent No. 0 227 826).

It may be convenient to change the order of the alkylation reaction (d or e) and the photoisomerisation reaction (g), in which case the (5Z)-isomer of I, Ia, II, or III is a key intermediate.

The side chain building blocks, RZ, are either known compounds (several are described in international patent application PCT/DK89/00079) or may be prepared analogously to those described in PCT/DK89/00079. The R is typically -(Q)-[C(R$^1$)(R$^2$)]$_n$X$^1$ in which X$^1$ is a protected OH group, e.g. tetrahydropyranyloxy or trialkylsilyloxy. (Any such THP ethers RZ, which are not described in PCT/DK89/00079, are readily prepared from the corresponding alcohol).

The side chain building block HY—R are also known compounds or may be prepared by methods analogous to those used to prepare such known compounds.

As schematized above, at least for the 23-thia compounds the route does not exclude deferring the alkylation of a 23-thiol even as far as the last step (e.g. IX→Ia (Scheme 3)).

The compounds of formula I in which Y═S(O) or S(O$_2$) may conveniently be prepared via oxidation of a corresponding compound IV, V, VI, VII or I, in which Y═S, for example with hydrogen peroxide and sodium tungstate in aqueous methanol. (The diastereoisomeric sulfoxides (Y═S(O)) may be separated chromatographically).

The following standard abbreviations are used throughout this disclosure:

Me=methyl
Et=ethyl
Pr$^n$=n-propyl
Pr$^i$=isopropyl
Bu$^t$=tert-butyl
THP=tetra-hydro-4H-pyran-2-yl
THF=tetrahydrofuran
Ts=p-toluene-sulphonyl
TBA=tetra-(n-butyl)-ammonium
DMF=dimethyl-formamide.

Scheme 1
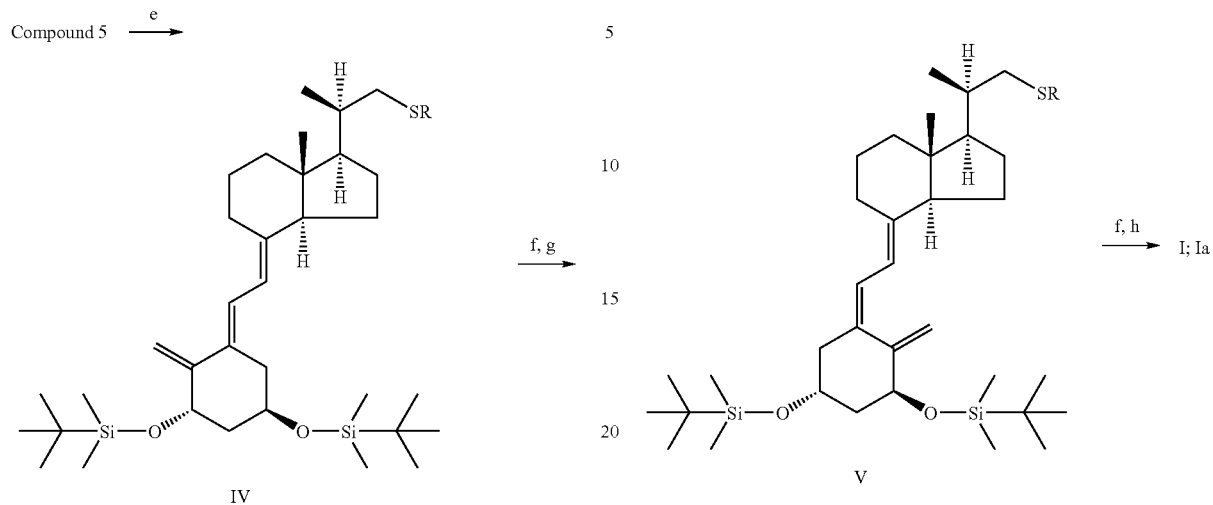
Scheme 2
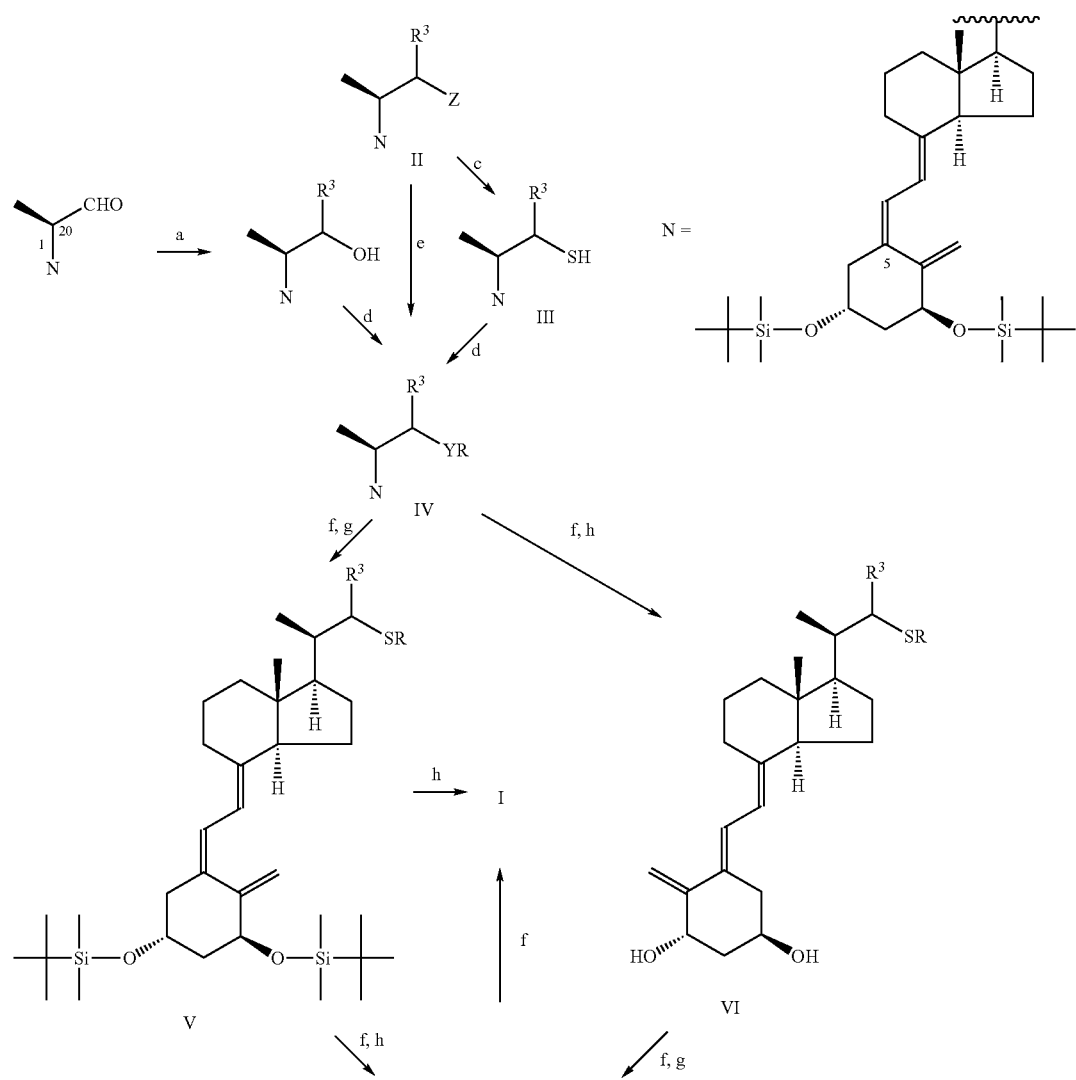

-continued

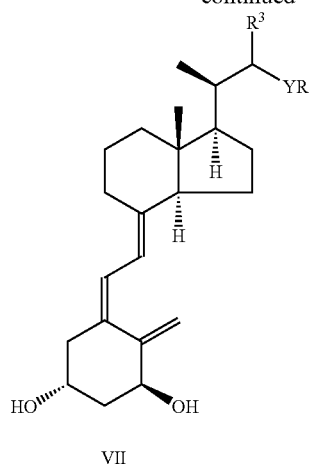

VII

Scheme 3

Compound 5 (R³ = H) or
Compound 90 (R³ = Me) or        g
Compound 91 (R³ = Me)       ——→
(see table 6)

VIII h
——→

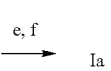

IX e, f
——→ Ia

Notes to Scheme 1, 2 and 3 a) Reaction with formal source of $R^3$ (e.g. reduction with $NaBH_4$ for $R^3$=H or reaction with $R^3Li$ for $R^3$=alkyl); optional separation of diastereoisomers for $R^3$=alkyl (e.g. by chromatography).
b) Conversion of OH to a leaving group (e.g. by tosylation for Z=OTs).
c) (i) Nucleophilic substitution with thioacetate, (ii) basic hydrolysis.
d) Alkylation with the side chain building block R-Z in the presence of base (e.g. KOH, KOBu$^t$ or KH), with or without catalyst (e.g. 18-Crown-6) in solvent (e.g.THF).
e) Reaction with the side chain building block R—YH in the presence of base (e.g. NaH) in solvent, e.g. DMF.
f) Optional functional group modification in the side chain.
g) Isomerisation with hv-triplet sensitizer, e.g. anthracene.
h) Deprotection with $TBA^+F$ or HF.

It should be noted that although the shown intermediates may have hydroxyl groups protected as tert-butyl-dimethylsilyl ethers, the scope of the invention does not exclude the use of alternative hydroxyl protecting groups well known in the art (such as those described in T. W. Greene and P. G. M. Wuts, "Protective groups in organic synthesis", 3$^{rd}$ ed., Wiley, New York, 1999), together with alternative reactions for deprotection.

The animals were divided into 6 groups:

Group 1: Intact control, dosed Propylene glycol 0.1 ml/kg (Vehicle)
Group 2: OVX rats control, dosed Propylene glycol 0.1 ml/kg (Vehicle)
Group 3: OVX rats, dosed 1α,25(OH)$_2$D$_3$, 0.25 µg/kg Group 4: OVX rats, dosed Compound 145, 10 μg/kg
Group 5: OVX rats, dosed Compound 145, 50 μg/kg
Group 6: OVX rats, dosed Compound 145, 100 μg/kg.

Figure 2:
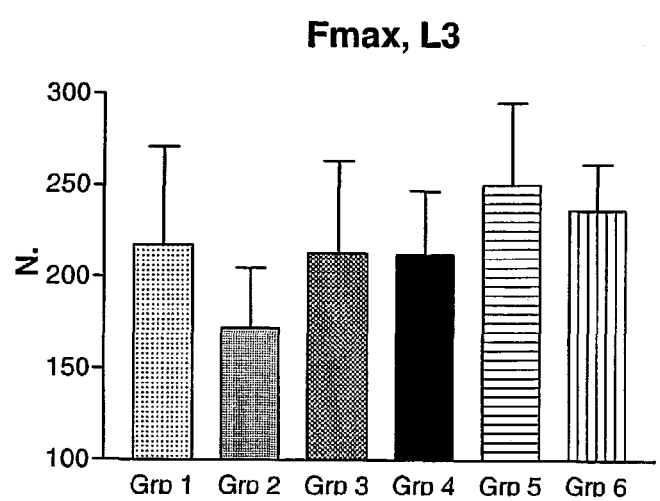

FIG. 2 is a graphic illustration of the biomechanical test of the lumbal vertebrae, L3. The vertebral body cylinder were tested along the proximal-distal axis in a materials testing machine (Alwetron TCT 5, Lorentzen and Wettre, Stockholm, Sweden) at a constant deformation rate of 2 mm/min. During compression, load-deformation curves were recorded and stored on a PC (ProLinea 4/33, Compaq, USA). Fmax is the maximum point on the load deforming curve.

Figure 1:
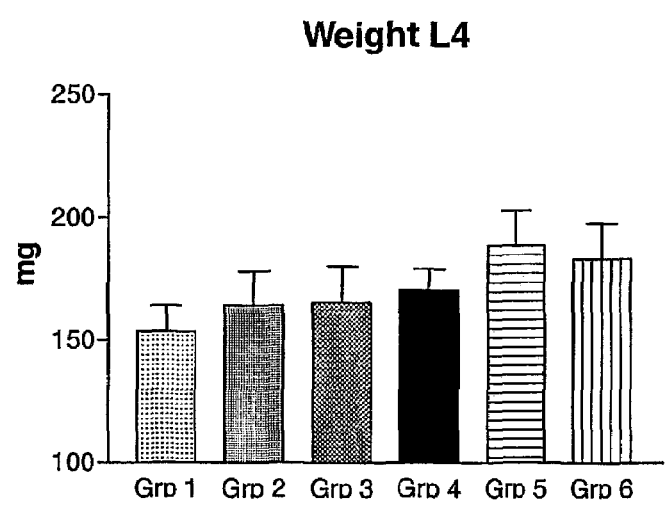
FIG. 1 is a graphic illustration of the effect on the weight of the lumbal vertebrae, L4, in rats according to the OVX rat model described herein, and wherein the animal groups received treatment according to the scheme below. A statistical analysis is shown below the graphic illustration. Differences between groups were investigated by the Kruskal-Wallis test, including a multiple comparison procedure: ns represents non-significant, nt represents not tested, and * represents $p<0.05$. Differences were considered significant at a $p<0.05$. Results are presented in the bar diagram as means+SD.

The rats were treated according to the OVX rat model described herein, and wherein the animal groups received treatment according to the same scheme as for FIG. 1. A statistical analysis is shown in the graphic illustration, cf. description for FIG. 1.

Pharmacological Methods—OVX Rat Model on Osteoporosis

To study bone anabolic properties and the effects of the vitamin D analogues of the present invention in preventing or treating demineralisation of the skeleton in vivo, a 4 weeks OVX rat model was used:

An ovariectomized rat model (OVX model), orally dosed for 28 days is useful for screening of vitamin D analogues. In this model ovariectomy produces alterations in the cancellous network identical to those seen in the human skeleton during ageing and the menopause. Besides this the model and the following analyses can be performed under very standardised conditions. $1\alpha,25(OH)_2D_3$ is used as a reference compound.

Animals and Diets:

Female Sprague Dawley rats weighing approximately 130 g (40–45 days old) were purchased from MB, Ejby, Denmark. The animals were fed a commercial diet and allowed free access to food and drinking water. The animals were split into groups receiving differential treatment.

Ovariectomy Procedure:

The animals were anaesthetised and ovariectomized through a dorsal incision.

Treatment of OVX animals was started 2 weeks after ovariectomy.

The animals were dosed orally for 28 days. The oral dosage was by gavage 0.1 ml/100 g bodyweight. The bodyweight of each animal was recorded every day prior to oral dosing. On day 7, 14, 21 and 28 the animals were housed separately for 24 hours in metabolic cages for collection of urine. Urine was frozen at −20° C. for later calcium measurement.

At day 28 the animals were anaesthetised and 2 ml of blood was obtained either by heart puncture or from the orbital vein, after this the animals were euthanized by $CO_2$. The serum fraction was then removed and frozen at −20° C. for later measurement of calcium, phosphorous and creatinine.

Uterus was removed and weighed to confirm the ovariectomy. Spleen and thymus were removed and weighed for evaluation of general immunological status.

Left and right femur, left and right tibia, lumbal vertebrae 3 and 4 (L3 and L4) were removed and cleaned for all soft- and connecting tissue. Left femur, left and right tibia and L4 were dried in an oven at 50–60° C. for at least 24 hours and immediately hereafter weighed. The bones were burned in an oven at 800° C. for 4 hours, dissolved in 1N HCl, and analysed for calcium content in a Hitachi 911 autoanalyser. Right femur and L3 were kept in 0.9% NaCl and frozen at −20° C. for later biomechanical testing performed by Jesper Skovhus Thomsen and Lis Mosekilde at Aarhus University, measuring various biomechanical parameters.

Effect of Compound 145 compared to the reference dose of $1,25(OH)_2D_3$ ($1,25D_3$) (0.25 μg/kg) and compared to the OVX control group (shown in %) are shown in Tables 1 to 4.

TABLE 1

Effect on urine calcium

| Comp. 145 | 1 μg/kg | 10 μg/kg | 25 μg/kg | 50 μg/kg | 75 μg/kg | 100 μg/kg |
|---|---|---|---|---|---|---|
| Vs | MTR/16 | MTR/16 | MTR/23 | MTR/27 | MTR/23 | MTR/27 | MTR/27 | MTR/23 |
| $1,25D_3$ | No | <<< | <<< | << | <= | = | >= | <= |
| Ovx contr | −23 | 104 | 45 | 155 | 373 | 750 | 777 | 463 |

TABLE 2

Effect on serum calcium

| Comp. 145 | 1 μg/kg | 10 μg/kg | 25 μg/kg | 50 μg/kg | 75 μg/kg | 100 μg/kg |
|---|---|---|---|---|---|---|
| Vs | MTR/16 | MTR/16 | MTR/23 | MTR/27 | MTR/23 | MTR/27 | MTR/27 | MTR/23 |
| $1,25D_3$ | No | No | < | < | No | = | = | No |
| Ovx contr | 0 | 3 | 6 | 11 | 2 | 18 | 20 | −5 |

TABLE 3

Anabolic effect on boneweight

| | Comp. 145 | 1 µg/kg | 10 µg/kg | 25 µg/kg | 50 µg/kg | | 75 µg/kg | 100 µg/kg |
|---|---|---|---|---|---|---|---|---|
| | Vs | MTR/16 | MTR/16 | MTR/23 | MTR/27 | MTR/23 | MTR/27 | MTR/23 |
| Femur | $1,25D_3$ | <= | > | >= | > | >> | > | > | > |
| | Ovx contr | 6 | 10 | 5 | 4 | 14 | 6 | 8 | 9 |
| Tibia | $1,25D_3$ | <= | > | >= | > | >> | > | > | > |
| | Ovx contr | 6 | 8 | 5 | 3 | 13 | 4 | 7 | 7 |
| Tibial Meta. | $1,25D_3$ | < | > | < | > | = | > | >> | = |
| | Ovx contr | 6 | 14 | 8 | −2 | 22 | −1 | 9 | 24 |
| L4 | $1,25D_3$ | <= | > | >= | > | >> | > | > | > |
| | Ovx contr | 9 | 13 | 4 | 9 | 15 | 11 | 13 | 12 |

TABLE 4

Effect on bone strength

| | Comp. 145 | 1 µg/kg | 10 µg/kg | 25 µg/kg | 50 µg/kg | | 75 µg/kg | 100 µg/kg |
|---|---|---|---|---|---|---|---|---|
| | Vs | MTR/16 | MTR/16 | MTR/23 | MTR/27 | MTR/23 | MTR/27 | MTR/23 |
| Femor. Dia. | $1,25D_3$ | <= | = | <= | > | = | > | > | = |
| | Ovx contr | | | −5 | 9 | −1 | 5 | 4 | −3 |
| Femor. Meta. | $1,25D_3$ | < | = | < | > | > | > | >> | = |
| | Ovx contr | | | 6 | 39 | 43 | 31 | 50 | 21 |
| L3 | $1,25D_3$ | < | > | = | <= | > | < | = | > |
| | Ovx contr | | | 23 | 27 | 45 | 22 | 38 | 37 |

< less effect than the reference dose of $1,25D_3$ (0.25 ug/kg)
<= less or the same effect as the reference dose of $1,25D_3$ (0.25 ug/kg)
= same effect as the reference dose of $1,25D_3$ (0.25 ug/kg)
=> same or better effect as the reference dose of $1,25D_3$ (0.25 ug/kg)
> better effect than the reference dose of $1,25D_3$ (0.25 ug/kg)

It appears from Tables 1 to 4 and FIG. 1 and FIG. 2 that the bone anabolic effects of the Compound 145 are comparable to or even better than $1,25D_3$, demonstrated by increased boneweight (FIG. 1) and an increase in the biomechanical strength of the bones (FIG. 2), whereas the adverse effect, the calcaemic effect, is reduced, which demonstrate the true anabolic effect of the compound. Thus, the present compounds are especially useful in the preparation of pharmaceutical compositions for the treatment of specific human and veterinary disorders as specified herein.

Pharmaceutical Formulations

While it is possible to administer the active ingredient alone (i.e. as the raw chemical), it is preferable to present it as a pharmaceutical formulation. Conveniently, the active ingredient comprises from 0.1 ppm to 1% by weight of the formulation.

Formulations, both for veterinary and for human medical use, of the present invention thus comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include e.g. those in a form suitable for oral, ophthalmic, rectal, parenteral (including subcutaneous, intramuscular and intravenous), transdermal, intra-articular and topical, nasal or buccal administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy, cf. *Remington: The Science and Practice of Pharmacy*, 19th Ed. 1995. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. It is preferred to dissolve or suspend the active compound in a non-aqueous liquid, such as vegetable oil, to be encapsulated in a gelatine capsule. The active ingredient may also be administered in the form of a bolus, electuary or paste.

Formulations for rectal administration may be in the form of a suppository incorporating the active ingredient and a carrier, or in the form of an enema.

Formulations suitable for parenteral administration conveniently comprise a sterile oily or aqueous preparation of the active ingredient which is preferably isotonic with the blood of the recipient. Transdermal formulations may be in the form of a plaster.

Formulations suitable for intra-articular or ophthalmic administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Tablet or capsule formulations are generally preferred for systemic administration of the active ingredient. A tablet formulation may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

For nasal administration or administration by inhalation of powder, self-propelling or spray formulations, dispensed with a spray can, a nebulizer or an atomizer can be used. The formulations, when dispensed, preferably have a particle size in the range of 10μ to 100μ. Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more medically acceptable inert gases or mixtures thereof. Generally, the propellant constitutes 45 to 99.9% w/w of the formulation whilst the active ingredient constitutes 1 ppm to 1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like.

As indicated above, compounds of formula I or Ia may be used in the treatment or prevention of osteoporosis or related bone disorders. Accordingly, the invention also relates to a method for the treatment of osteoporosis and related conditions comprising administering to a patient in need thereof an effective amount of a compound of formula I or Ia.

Furthermore, the invention relates to the use of compounds of formula Ia in pharmaceutical compositions for the local or systemic treatment or prophylaxis of human and veterinary disorders amenable to treatment with vitamin D or vitamin D analogues, such as e.g. psoriasis and other disturbances of keratinization, HIV-associated dermatoses, wound healing, various cancer forms, such as leukemia, mammary cancer, brain glial tumours, osteosarcoma, myelofibrosis, melanoma, other skin cancers, and of diseases of, or imbalances in, the immune system, such as host versus graft and graft versus host reaction and transplant rejection, and autoimmune diseases, such as discoid and systemic lupus erythematosus, diabetes mellitus and chronic dermatoses of autoimmune type, e.g. scleroderma and pemphigus vulgaris, and inflammatory diseases, such as asthma and rheumatoid arthritis, as well as a number of other disease states including hyperparathyroidism, particularly secondary hyperparathyroidism associated with renal failure, cognitive impairment or senile dementia (Alzheimers disease) and other neurodegenerative diseases, hypertension, acne, alopecia, skin atrophy, e.g. steroid induced skin atrophy, skin ageing, including photo-ageing, and to their use for promoting osteogenesis and treating/preventing osteoporosis and related bone disorders and osteomalacia. Moreover, the bone anabolic activity of the novel compounds of the invention is accompanied by a strengthening effect on the skeletal muscles.

The amount required of a compound of formulae I or Ia for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

The present compounds may be used in combination with other pharmaceuticals or treatment modalities. In the treatment of osteoporosis, they may suitably be combined with other therapeutic agents for the treatment or prevention of osteoporosis, including estrogens, SERMs (selective estrogen receptor modulators) or bisphosphonates. In the treatment of psoriasis the present compounds may be used in combination with other antipsoriatic drugs, e.g. steroids, or with other treatments e.g. light- or UV-light-treatment or the combined PUVA-treatment. In the treatment of cancer the present compounds may be used in combination with other anti-cancer drugs or anti-cancer treatments, such as radiation treatment. In the prevention of graft rejection and graft versus host reaction, or in the treatment of auto-immune diseases, the present compounds may advantageously be used in combination with other immunosuppressive/immunoregulating drugs or treatments, e.g. with cyclosporin A.

The present invention further relates to a method for treating patients suffering from one of the above pathological conditions, said method consisting of administering to a patient in need of treatment an effective amount of one or more compounds of formulae I or Ia, alone or in combination with one or more other therapeutically active compounds usually applied in the treatment of said pathological conditions. The treatment with the present compounds and/or with further therapeutically active compounds may be simultaneous or at intervals. Preferred pathological conditions to be treated with the present compounds are steroid induced, senile, and postmenopausal osteoporosis.

For systemic treatment, daily doses of from 0.001–100 μg per kg body weight, preferably from 0.01–50 μg/kg of mammal body weight, for example 0.05–30 μg/kg of a compound of formula I or Ia are administered, typically corresponding to a daily dose for an adult human of from about 0.5 μg to about 6 mg. In the topical treatment of dermatological disorders, ointments, creams or lotions containing from 0.1–500 μg/g, and preferably from 0.1–100 μg/g, of a compound of formula I or Ia are administered. For topical use in ophthalmology ointments, drops or gels containing from 0.1–500 μg/g, and preferably from 0.1–100 μg/g, of a compound of formula I or Ia are administered. The oral compositions are formulated, preferably as tablets, capsules, or drops, containing from 0.05–50 μg, preferably from 0.1–25 μg, of a compound of formula I or Ia, per dosage unit.

The invention is further described in the following Preparations and Examples which are not in any way intended to limit the scope of the invention as claimed.

PREPARATIONS AND EXAMPLES

General

The exemplified compounds Ia are listed in Table 5. The intermediates of Scheme 1, 2 and 3 referred to in the Preparations are to be identified by numbers with the corresponding formulae in Table 6. These are used to illustrate typical syntheses of the exemplified compounds Ia.

For $^1$H nuclear magnetic resonance spectra (300 MHz) chemical shift values (δ) are quoted in ppm for deuteriochloroform solutions (except where otherwise stated) relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit. For $^{13}$C nuclear magnetic resonance spectra (75.5 MHz) chemical shift values (δ) are quoted in ppm for deuteriochloroform solutions (except where otherwise stated) relative to internal tetramethylsilane (δ=0) or chloroform (δ=76.81).

Ether is diethyl ether, and was dried over sodium. THF was dried over sodium-benzophenone. Petroleum ether refers to the pentane fraction. If not specified, % means v/v %. Reactions were run at room temperature unless otherwise noted. The work-up procedure referred to involves dilution with the specified solvent (otherwise the organic reaction solvent), extraction with water and then brine, drying over anhydrous MgSO$_4$, and concentration in vacuo to give a residue. Chromatography was performed on silica gel.

TABLE 5

Examples of Compounds of formula Ia wherein n = 0 (Compound 147, 148, 149) or n = 1. (Compounds 101 to 154 of formula I are listed in the corresponding Table 1 disclosed in WO 91/15475 incorporated herein by reference). Details are provided for compounds where an Example No. is given; other compounds may be prepared using analogous reaction sequences from known starting materials.

| Compound No. | Example No. | R3 | m | Q | R1 | R2 |
|---|---|---|---|---|---|---|
| 142 | 1 | H | 0 | ortho-C$_6$H$_4$ | Me | Me |
| 144 | 2 | H | 0 | meta-C$_6$H$_4$ | Et | Et |
| 145 | 3 | H | 0 | para-C$_6$H$_4$ | Me | Me |
| 147 | 4 | H | 0 | ortho-C$_6$H$_4$ | — | — |
| 148 | 5 | H | 0 | meta-C$_6$H$_4$ | — | — |
| 149 | 6 | H | 0 | para-C$_6$H$_4$ | — | — |
| 155 | 7 | H | 0 | (CH$_2$)$_2$CF$_2$ | Me | Me |
| 156 | 8 | H | 1 | (CH$_2$)$_2$CF$_2$ | Me | Me |
| 157Ω | 9 | H | 1 | meta-C$_6$H$_4$ | Me | Me |
| 158 | 10 | H | 2 | meta -C$_6$H$_4$ | Me | Me |
| 159ΩΩ | 11 | H | 1 | meta-C$_6$H$_4$ | Me | Me |
| 160 | 12 | H | 2 | para-C$_6$H$_4$ | Me | Me |
| 161Φ | 13 | H | 1 | para-C$_6$H$_4$ | Me | Me |
| 162ΦΦ | 14 | H | 1 | para-C$_6$H$_4$ | Me | Me |
| 163 | 15 | H | 0 | para-C$_6$H$_4$ | H | H |
| 164 | 16 | H | 0 | para-C$_6$H$_4$ | Et | Et |
| 165θ | 17 | Me | 0 | para-C$_6$H$_4$ | Me | Me |
| 166θθ | 18 | Me | 0 | para-C$_6$H$_4$ | Me | Me |

ΩIsomer with compound 159
ΩΩIsomer with compound 157
ΦIsomer with compound 162
ΦΦIsomer with compound 161
θIsomer with compound 166
θθIsomer with compound 165

TABLE 6

Intermediate compounds used in the synthesis of compounds of formula I or Ia (Compounds 2 to 66 are listed in the corresponding Table 2 disclosed in WO 91/15475 and prepared according to Preparations 1 to 64 and General Procedures 1 to 7 disclosed in WO 91/15475 incorporated herein by reference).

| | | Formula | | |
|---|---|---|---|---|
| Compound No. | Prep No. | Type (See Scheme 2 + 3) | R3 | YR or Z |
| 67 | 1 | V | H | S—(CH$_2$)$_2$CF$_2$—C(OSiMe$_3$)Me$_2$ |
| 68 | 2 | IV | H | S—(CH$_2$)$_2$CF$_2$—C(OSiMe$_3$)Me$_2$ |
| 70# | 4 | V | H | S(O)-meta-C$_6$H$_4$—C(OH)Me$_2$ |
| 71 | 5 | V | H | S(O$_2$)-meta-C$_6$H$_4$—C(OH)Me$_2$ |
| 72## | 4 | V | H | S(O)-meta-C$_6$H$_4$—C(OH)Me$_2$ |
| 73 | 6 | V | H | S(O$_2$)-para-C$_6$H$_4$—C(OH)Me$_2$ |
| 74 | 7 | V | H | S-para-C$_6$H$_4$—C(OH)Me$_2$ |

TABLE 6-continued

Intermediate compounds used in the synthesis of compounds of formula I or Ia (Compounds 2 to 66 are listed in the corresponding Table 2 disclosed in WO 91/15475 and prepared according to Preparations 1 to 64 and General Procedures 1 to 7 disclosed in WO 91/15475 incorporated herein by reference).

| | | Formula | | |
|---|---|---|---|---|
| Compound No. | Prep No. | Type (See Scheme 2 + 3) | R3 | YR or Z |
| 75□ | 8 | V | H | S(O)-para-$C_6H_4$—$C(OH)Me_2$ |
| 76□□ | 8 | V | H | S(O)-para-$C_6H_4$—$C(OH)Me_2$ |
| 77 | 9 | V | H | S-ortho-$C_6H_4$—$C(OH)Me_2$ |
| 78 | 10 | V | H | S-ortho-$C_6H_4$—COOMe |
| 79 | 11 | IV | H | S-ortho-$C_6H_4$—COOMe |
| 80 | 12 | V | H | S-meta-$C_6H_4$—$C(OH)Et_2$ |
| 81 | 13 | IV | H | S-meta-$C_6H_4$—$C(OH)Et_2$ |
| 82 | 14 | IV | H | S-para-$C_6H_4$—$C(OH)Me_2$ |
| 83 | 15 | V | H | S-ortho-$C_6H_4$—OH |
| 84 | 16 | IV | H | S-ortho-$C_6H_4$—OH |
| 85 | 17 | V | H | S-meta-$C_6H_4$—OH |
| 86 | 18 | IV | H | S-meta-$C_6H_4$—OH |
| 87 | 19 | VIII | H | — |
| 88 | 20 | V | H | S-para-$C_6H_4$—OH |
| 89 | 21 | IX | H | — |
| 90ω | 22 | II | Me | OTs |
| 91ωω | 23 | II | Me | OTs |
| 92ⓢ | 24 | VIII | Me | — |
| 93ⓢ | 25 | VIII | Me | — |
| 94θ | 26 | IX | Me | — |
| 95θθ | 27 | IX | Me | — |

Isomer with compound 72
Isomer with compound 70
□Isomer with compound 76
□□Isomer with compound 75
ωIsomer with compound 91.
ωωIsomer with compound 90.
ⓢ Isomer with compound 93.
ⓢ ⓢ Isomer with compound 92.
θIsomer with compound 95.
θθIsomer with compound 94.

Preparations

Preparation 1: Compound 67
  Method: General Procedure 3.
  Compound IV: Compound 68.
  Chromatography eluant: 0–4% ethyl acetate in petroleum ether.
  $^{13}$C NMR: δ=148.1, 140.4, 135.0, 123.9, 122.9, 117.9, 111.0, 75.6, 71.9, 67.3, 55.9, 55.6, 45.8, 45.5, 44.6, 40.4, 39.2, 35.6, 31.8, 28.6, 26.9, 25.8, 25.7, 25.6, 24.1, 23.3, 21.8, 18.6, 18.0, 17.9, 12.3, 2.1, −4.9, −5.0, −5.3.

Preparation 2: Compound 68
  Method: General Procedure 2, but replacing DMF with THF/hexamethylphosphoric triamide 20:1 (v/v).
  Compound II: Compound 5.
  R—YH: Compound 69.
  $^{13}$C NMR: δ=153.4, 142.7, 135.4, 123.9, 121.5, 116.4, 106.5, 75.6, 70.0, 67.0, 56.1, 55.6, 45.6, 43.8, 40.3, 39.2, 36.4, 35.6, 31.8, 28.7, 26.9, 25.6, 24.8, 24.1, 23.3, 21.9, 18.6, 18.1, 17.9, 12.3, 2.1, −4.9, −5.1, −5.1.

Preparation 3: Compound 69

3,3-difluoro-4-methyl-4-(trimethylsilyloxy)pentanethiol
  Method: Methylmagnesium bromide (3 M, 2 equiv.) in ether was added to 4-bromo-2,2-difluorobutanoate (D. Morel and F. Dawans, Tetrahedron, 33, 1445–7, (1977)) in ether. Work up gave 5-bromo-3,3-difluoro-2-methyl-propan-2-ol. $^{13}$C NMR: δ=123.9, 72.8, 35.2, 23.4, 23.1. Treatment of this compound (2.0 g), triethylamine (1.70 mL) and 4-(dimethylamino)-pyridine (59 mg) in dichloromethane (25 mL) with trimethylsilylchloride (1.52 mL) at room temperature over night gave after work up with dichloromethane and chromatography (1–3% ethyl acetate in petroleum ether as eluant) 1-bromo-3,3-difluoro-4-methyl-4-(trimethylsilyloxy)-pentane. $^{13}$C NMR: δ=123.6, 75.5, 35.2, 24.2, 23.9, 2.1. This compound (1.62 g) was reacted with potassium O-ethyl xantogenate (1.80 g) in acetone (15 mL) at room temperature over night and worked up with chloroform/saturated aqueous ammonium chloride to give S-(3,3-difluoro-4-methyl-4-(trimethylsilyloxy)-pentyl)-O-ethyl xantogenate. $^{13}$C NMR: δ=214.0, 123.7, 75.6, 69.7, 30.5, 28.2, 24.0, 13.5, 2.1. This compound (0.6 g) was reacted with ethanolamine (0.22 mL) in DMF (5 mL) for 30 min at room temperature and worked up with water/ether. Chromatography (ether/petroleum ether 1:100 as eluant) gave Compound 69. $^{13}$C NMR: δ=123.9, 75.5, 35.8, 24.0, 17.0, 2.1.

Preparation 4: Compound 70 and 72
  The compounds were prepared using the method of Preparation 41 of WO 91/15475, except using compound 57 as starting material instead of compound 15.
  Compound 70, lowest Rf, $^{13}$C NMR: δ=150.8, 148.1, 144.1, 139.8, 135.3, 128.8, 127.4, 122.9, 122.7, 120.1, 118.0, 110.9, 72.3, 71.8, 67.3, 65.3, 55.7, 45.8, 45.3, 44.6, 40.3, 31.7, 31.6, 31.3, 28.5, 26.1, 25.6, 25.6, 23.1, 21.5, 19.5, 18.0, 17.9, 12.0, −4.9, −5.0, −5.3.
  Compound 72, highest Rf, $^{13}$C NMR: δ=150.6, 148.1, 144.7, 139.8, 135.3, 129.0, 126.9, 122.7, 122.0, 119.8, 118.1, 111.0, 72.3, 71.9, 67.3, 65.6, 56.2, 55.9, 45.9, 45.5, 44.6, 40.6, 31.7, 31.6, 31.0, 28.5, 26.9, 25.7, 25.6, 23.1, 21.6, 18.7, 18.0, 17.9, 12.3, −4.9, −5.0, −5.3.

Preparation 5: Compound 71
  The compound was prepared using the method of Preparation 42 of WO 91/15475, except using compound 57 as starting material instead of compound 43 and/or 44.
  $^{13}$C NMR: δ=150.8, 148.1, 139.9, 139.6, 135.4, 129.6, 129.0, 126.1, 123.7, 122.7, 118.1, 111.0, 72.2, 71.8, 67.3, 61.6, 55.8, 55.6, 45.8, 45.3, 44.6, 40.4, 31.7, 30.5, 29.5, 28.4, 26.3, 25.6, 25.6, 23.1, 21.3, 19.4, 18.0, 17.9, 12.1, −4.9, −5.0, −5.3.

Preparation 6: Compound 73
  The compound was prepared using the method of Preparation 42 of WO 91/15475, except using compound 74 as starting material instead of compound 43 and/or 44.
  $^{13}$C NMR: δ=155.0, 148.1, 139.6, 138.3, 135.4, 127.7, 125.2, 122.7, 118.1, 111.0, 72.3, 71.8, 67.3, 61.7, 55.9, 55.7, 45.8, 45.3, 44.6, 40.4, 31.6, 30.4, 28.5, 26.3, 25.6, 25.6, 23.1, 21.3, 19.4, 18.0, 17.9, 12.0, −4.9, −5.0, −5.3.

Preparation 7: Compound 74
  Method: General Procedure 3.
  Starting material: Compound 82.
  Chromatography eluant: 0 to 50% ether in petroleum ether.
  $^{13}$C NMR: δ=148.1, 146.5, 140.3, 135.7, 135.1, 128.8, 124.8, 122.9, 117.9, 111.0, 72.1, 71.8, 67.3, 55.9, 55.6, 45.8, 45.5, 44.6, 40.8, 40.3, 35.2, 31.5, 28.6, 26.8, 25.7, 25.6, 23.3, 21.7, 18.7, 18.0, 17.9, 12.2, −4.9, −5.0, −5.3.

Preparation 8: Compound 75 and 76
  The compounds were prepared using the method of Preparation 41 of WO 91/15475, except using compound 74 as starting material instead of compound 15.
  Compound 75, highest Rf, $^{13}$C NMR: δ=152.1, 148.1, 142.7, 139.8, 135.3, 125.3, 123.7, 122.7, 118.1, 111.0, 72.1, 71.9, 67.3, 65.6, 56.2, 55.9, 45.9, 45.5, 44.6, 40.6, 31.6, 31.0, 28.5, 27.0, 25.6, 25.6, 23.1, 21.6, 18.7, 18.0, 17.9, 12.3, −4.9, −5.0, −5.3.

Compound 76, lowest Rf, $^{13}$C NMR: δ=152.8, 148.1, 142.2, 139.8, 135.2, 125.2, 124.3, 122.7, 118.0, 110.9, 72.2, 71.8, 67.3, 65.3, 55.7, 55.7, 45.8, 45.3, 44.6, 40.3, 31.6, 31.2, 28.5, 26.0, 25.6, 25.6, 23.1, 21.5, 19.5, 18.0, 17.9, 12.0, −4.9, −5.0, −5.3.

Preparation 9: Compound 77
Method: General Procedure 7.
Starting material: Compound 78.
$^{1}$H NMR: δ=7.42(m, 2H), 7.17(m, 2H), 6.22(d, 1H), 6.00(d, 1H), 5.17(d, 1H), 4.89(s, 1H), 4.85(d, 1H), 4.36(m, 1H), 4.18(m, 1H), 3.25(dd, 1H), 2.88(dd, 1H), 2.83(dd, 1H), 2.43(dd, 1H), 2.20(dd, 1H), 1.99(t, 1H), 1.68(s, 6H), 1.90–1.20(m, 13H), 1.08(d, 3H), 0.86(s, 18H), 0.86(s, 18H), 0.15(s, 3H), 0.05(s, 12H).

Preparation 10: Compound 78
Method: General Procedure 3.
Starting material: Compound 79.
Chromatography eluant: 0 to 20% ether in petroleum ether.
$^{1}$H NMR: δ=7.92(d, 1H), 7.41(t, 1H), 7.28(d, 1H), 7.10(t, 1H), 6.22(d, 1H), 6.02(d, 1H), 5.17(d, 1H), 4.85(d, 1H), 4.35(m, 1H), 4.17(m, 1H), 3.81(s, 3H), 3.19(dd, 1H), 2.82(dd, 1H), 2.72(dd, 1H), 2.43(dd, 1H), 2.20(dd, 1H), 1.98(t, 1H), 1.95–1.30(m, 13H), 1.08(d, 1H), 0.90(s, 18H), 0.56(s, 3H), 0.05(s, 12H).

Preparation 11: Compound 79
Method: General Procedure 2.
Compound II: Compound 5.
R—YH: Methyl 2-mercaptobenzoate.
$^{1}$H NMR: δ=7.93(d, 1H), 7.41(t, 1H), 7.28(d, 1H), 7.13(t, 1H), 6.44(d, 1H), 5.82(d, 1H), 4.97(d, 1H), 4.93(d, 1H), 4.51(dd, 1H), 4.21(m, 1H), 3.91(s, 1H), 3.19(dd, 1H), 2.87(d, 1H), 2.73(dd, 1H), 2.55(dd, 1H), 2.31(d, 1H), 2.07(t, 1H), 1.95–1.35(m, 15H), 1.09(d, 1H), 0.89(s, 9H), 0.85(s, 9H), 0.57(s, 3H), 0.05(s, 12H).

Preparation 12: Compound 80
Method: General Procedure 3.
Starting material: Compound 81.
Chromatography eluant: 0 to 20% ether in petroleum ether.
$^{13}$C NMR: δ=148.1, 146.3, 140.3, 137.0, 135.0, 128.2, 127.1, 126.5, 123.0, 122.9, 117.9, 111.0, 71.9, 67.3, 55.9, 55.6, 45.8, 45.5, 44.6, 40.9, 40.3, 35.3, 34.8, 28.6, 26.8, 25.7, 25.6, 23.2, 21.7, 18.6, 18.0, 18.0, 12.3, 7.6, −4.9, −5.0, −5.3.

Preparation 13: Compound 81
Method: General Procedure 2.
Compound II: Compound 5.
R—YH: 3-(3-mercaptophenyl)pentan-3-ol (cf. G. Grue-Sørensen, E. Binderup and L. Binderup, in "Vitamin D, a pluripotent steroid hormone: Structural studies, molecular endocrinology and clinical applications", Eds. A. W. Norman, R. Bouillon and M. Thomaset, Walter de Gruyter, New York, 1994, p. 75–76).
$^{13}$C NMR: δ=153.4, 146.3, 142.7, 137.0, 135.4, 128.2, 127.1, 126.5, 123.0, 121.5, 116.4, 106.5, 70.0, 67.0, 56.0, 55.6, 45.6, 43.8, 40.9, 40.2, 36.4, 35.3, 34.8, 28.7, 26.7, 25.7, 25.6, 23.3, 22.1, 21.8, 18.6, 18.1, 17.9, 12.3, 7.6, −5.0, −5.1, −5.1.

Preparation 14: Compound 82
Method: General Procedure 2.
Compound II: Compound 5.
R—YH: 2-(4-mercaptophenyl)propan-2-ol (cf. G. Grue-Sørensen, E. Binderup and L. Binderup, in "Vitamin D, a pluripotent steroid hormone: Structural studies, molecular endocrinology and clinical applications", Eds. A. W. Norman, R. Bouillon and M. Thomaset, Walter de Gruyter, New York, 1994, p. 75–76).
$^{13}$C NMR: δ=153.4, 146.5, 142.6, 135.7, 135.4, 128.8, 124.8, 121.4, 116.4, 106.5, 72.1, 70.1, 67.0, 56.0, 55.6, 45.6, 43.7, 40.8, 40.2, 36.4, 35.2, 31.5, 28.7, 26.8, 25.7, 25.6, 23.3, 21.8, 18.7, 18.0, 17.9, 12.3, −5.0, −5.1, −5.1.

Preparation 15: Compound 83
Method: General Procedure 3.
Starting material: Compound 84.
Chromatography eluant: 0 to 20% ether in petroleum ether.
$^{1}$NMR: δ=7.44(d, 1H), 7.22(t, 1H), 6.96(d, 1H), 6.87(t, 1H), 6.72(s, 1H), 6.19(d, 1H), 5.98(d, 1H), 5.15(d, 1H), 4.83(d, 1H), 4.35(t, 1H), 4.15(m, 1H), 2.98(dd, 1H), 2.79(dd, 1H), 2.56(dd, 1H), 2.4(dd, 1H), 2.18(dd, 1H), 2.03(t, 1H), 1.95–1.3(m, 13H), 1.05(d, 3H), 0.88(s, 18), 0.34(s, 3H), 0.03(m, 12H).

Preparation 16: Compound 84
Method: General Procedure 2. The reaction conditions were changed from 30 min and room temperature to 10 min and 60° C.
Compound II: Compound 5.
R—YH: 2-mercaptophenol (a 10-fold molar excess over Compound 5 was used).
$^{1}$H NMR: δ=7.45(d, 1H), 7.22(t, 1H), 6.96(d, 1H), 6.65(t, 1H), 6.73(s, 1H), 6.42(d, 1H), 5.79(d, 1H), 4.97(t, 1H), 4.92(t, 1H), 4.51(dd, 1H), 4.20(m, 1H), 2.98(dd, 1H), 2.84(dd, 1H), 2.56(dd, 1H), 2.50(d, 1H), 2.29(d, 1H), 2.00(t, 1H), 1.95–1.3(m, 13H), 1.06(d, 3H), 0.89(s, 9H), 0.84(s, 9H), 0.35(s, 3H), 0.05(m, 12H).

Preparation 17: Compound 85
Method: General Procedure 2. Compound II was replaced with compound 87. The reaction conditions were changed from 30 min and room temperature to 10 min and 60° C.
R—YH: 3-mercaptophenol (a 10-fold molar excess over Compound 87 was used).
Chromatography eluant: 0 to 20% ether in petroleum ether.
$^{13}$C NMR: δ=155.6, 148.1, 140.3, 139.3, 135.0, 129.6, 122.9, 120.8, 117.9, 115.2, 112.4, 111.0, 71.8, 67.4, 55.9, 55.6, 45.8, 45.5, 44.6, 40.3, 35.2, 28.6, 26.8, 25.7, 25.6, 23.3, 21.8, 18.7, 18.0, 18.0, 12.3, −4.9, −5.0, −5.3.

Preparation 18: Compound 86
Method: General Procedure 2. The reaction conditions were changed from 30 min and room temperature to 10 min and 60° C.
Compound II: Compound 5.
R—YH: 3-mercaptophenol (a 10-fold molar excess over Compound 5 was used).

Preparation 19: Compound 87
Method: General Procedure 3.
Starting material: Compound 5.
Chromatography eluant: 10% ether in petroleum ether.
$^{13}$C NMR: δ=148.1, 144.4, 139.9, 135.2, 133.1, 129.5, 127.7, 122.8, 118.0, 111.0, 74.1, 71.8, 67.3, 55.7, 52.2, 45.8, 45.1, 44.6, 39.6, 35.2, 28.5, 26.6, 25.6, 25.6, 23.1, 21.7, 21.4, 18.0, 17.9, 16.5, 12.1, −4.9, −5.0, −5.3.

Preparation 20: Compound 88
Method: General Procedure 2. The reaction conditions were changed from 30 min and room temperature to 10 min and 60° C.
The compound of formula II was replaced by Compound 87.

R—YH: 4-mercaptophenol (a 10-fold molar excess over Compound 5 was used).

$^{13}$C NMR: δ=154.4, 148.1, 140.4, 135.0, 132.9, 127.7, 122.9, 117.9, 115.8, 111.0, 71.8, 67.4, 55.9, 55.5, 45.8, 45.5, 44.6, 42.9, 40.3, 35.4, 28.6, 26.8, 25.7, 25.6, 23.3, 21.7, 18.6, 18.0, 18.0, 12.2, −4.9, −5.0, −5.3.

Preparation 21: Compound 89
  Method: General Procedure 4.
  Starting material V was replaced by a compound of the general formula VIII: Compound 87.
  Compound 89 was purified by recrystallisation from ethyl acetate.

Preparation 22: Compound 90
  Method: The method used in preparation 3 of WO 91/15475 was used, but replacing compound 2 with compound 3.

Preparation 23: Compound 91
  Method: The method used in preparation 3 of WO 91/15475 was used, but replacing compound 2 with compound 4.

Preparation 24: Compound 92
  Method: General Procedure 3.
  Starting material: Compound 90.
  Chromatography eluant: 10% ether in petroleum ether.

Preparation 25: Compound 93
  Method: General Procedure 3.
  Starting material: Compound 91.
  Chromatography eluant: 10% ether in petroleum ether.

Preparation 26: Compound 94
  Method: General Procedure 4.
  Starting material V: Compound 92.

Preparation 27: Compound 95
  Method: General Procedure 4.
  Starting material V: Compound 93.

EXAMPLES

Example 1

1(S),3(R)-Dihydroxy-20(R)-(2-((1-hydroxy-1-methyl)ethyl)phenylthiomethyl)-9,10-seco-pregna-5(Z),7(E),10(19)-triene, Compound 142

Method: General Procedure 4.
Starting material V: Compound 77.
$^{1}$H NMR: δ=7.44(m, 2H), 7.19(m, 2H), 6.36(d, 1H), 6.02(d, 1H), 5.32(d, 1H), 4.99(s, 1H), 4.89(s, 1H), 4.42(m, 1H), 4.13(m, 1H), 3.25(dd, 1H), 2.88(dd, 1H), 2.82(dd, 1H), 2.58(dd, 1H), 2.30(dd, 1H), 2.05–1.25(m, 16H), 1.68(s, 6H), 1.08(d, 3H), 0.53(s, 3H).

Example 2

1(S),3(R)-Dihydroxy-20(R)-(3-((1-hydroxy-1-ethyl)propyl)phenylthiomethyl)-9,10-seco-pregna-5(Z),7(E),10(19)-triene, Compound 144

Method: General Procedure 4.
Starting material V: Compound 80.
$^{13}$C NMR: δ=147.7, 146.5, 142.7, 137.2, 133.1, 128.4, 127.3, 126.7, 124.9, 123.2, 117.2, 111.8, 70.8, 66.9, 56.1, 55.8, 45.8, 45.3, 42.9, 41.2, 40.3, 35.5, 35.0, 29.0, 26.8, 23.5, 22.1, 18.8, 12.5, 7.8.

Example 3

1(S),3(R)-Dihydroxy-20(R)-(4-((1-hydroxy-1-methyl)ethyl)phenylthiomethyl)-9,10-seco-pregna-5(Z),7(E),10(19)-triene, Compound 145

Method: General Procedure 4.
Starting material V: Compound 74.
$^{13}$C NMR: δ=147.7, 146.7, 142.6, 135.8, 133.2, 129.0, 125.0, 124.8, 117.3, 111.8, 72.3, 70.8, 66.8, 56.1, 55.8, 45.8, 45.2, 42.9, 41.0, 40.3, 35.4, 31.7, 29.0, 26.9, 23.5, 22.1, 18.9, 12.5.

Example 4

1(S),3(R)-Dihydroxy-20(R)-(2-hydroxy)phenylthiomethyl)-9,10-seco-pregna-5(Z),7(E),10(19)-triene, Compound 147

Method: General Procedure 4.
Starting material V: Compound 83.
$^{1}$H NMR: δ=7.45(d, 1H), 7.23(t, 1H), 6.97(d, 1H), 6.85(t, 1H), 6.74(s, 1H), 6.34(d, 1H), 5.98(d, 1H), 5.31(d, 1H), 4.97(d, 1H), 4.42(m, 1H), 4.21(m, 1H), 2.98(dd, 1H), 2.80(dd, 1H), 2.52(m, 2H), 2.29(dd, 1H), 2.0–1.20(m, 16H), 1.06(d, 3H), 0.35(s, 3H).

Example 5

1(S),3(R)-Dihydroxy-20(R)-(3-hydroxy)phenylthiomethyl)-9,10-seco-pregna-5(Z),7(E),10(19)-triene, Compound 148

Method: General Procedure 4.
Starting material V: Compound 85
$^{13}$C NMR: δ=155.8, 147.6, 142.7, 139.4, 133.1, 129.8, 125.0, 121.1, 117.2, 115.5, 112.7, 111.9, 70.9, 66.9, 56.1, 55.7, 45.8, 45.3, 42.9, 40.5, 40.3, 35.3, 29.0, 26.9, 23.6, 22.1, 18.9, 12.5.

Example 6

1(S),3(R)-Dihydroxy-20(R)-(4-hydroxy)phenylthiomethyl)-9,10-seco-pregna-5(Z),7(E),10(19)-triene, Compound 149

Method: General Procedure 4.
Starting material V: Compound 88.
$^{13}$C NMR: δ=154.8, 147.6, 142.8, 133.2, 133.0, 127.7, 125.0, 117.2, 116.0, 111.9, 70.9, 66.9, 56.2, 55.7, 45.8, 45.3, 43.1, 42.8, 40.4, 35.5, 29.0, 26.9, 23.6, 22.1, 18.7, 12.4.

Example 7

1(S),3(R)-Dihydroxy-20(R)-(3,3-difluoro-4-hydroxy-4-methyl-1-pentylthiomethyl)-9,10-seco-pregna-5(Z),7(E),10(19)-triene, Compound 155

Method: General Procedure 5.
Starting material V: Compound 67.
$^{13}$C NMR: δ=147.6, 142.7, 133.2, 124.9, 124.4, 117.3, 111.8, 73.1, 70.8, 66.8, 56.1, 55.7, 45.8, 45.3, 42.9, 40.4, 39.4, 35.7, 32.2, 29.0, 26.9, 24.8, 23.5, 23.5, 22.1, 18.8, 12.5.

Example 8

1(S),3(R)-Dihydroxy-20(R)-(3,3-difluoro-4-hydroxy-4-methyl-1-pentylsulphinylmethyl)-9,10-seco-pregna-5(Z),7(E),10(19)-triene, Compound 156

Method: As in Preparation 41 of WO 91/15475
Starting material I: Compound 155.
$^{13}$C NMR: δ=147.7, 142.1, 133.5, 126.1, 124.7, 117.5, 111.8, 73.1, 70.8, 66.8, 60.5, 58.5, 56.3, 56.0, 45.8, 45.3, 42.9, 40.4, 31.9, 28.9, 26.2, 23.5, 23.4, 22.0, 19.4, 18.4, 12.8.

Example 9

1(S),3(R)-Dihydroxy-20(R)-(3-((1-hydroxy-1-methyl)ethyl)phenylsulphinylmethyl)-9,10-seco-pregna-5(Z),7(E),10(19)-triene, Compound 157 (isomer with Compound 159)

Method: General Procedure 4.
Starting material V: Compound 70.
$^{13}$C NMR: δ=151.3, 147.7, 143.8, 141.9, 133.7, 129.0, 127.8, 124.5, 123.1, 120.4, 117.5, 111.7, 72.3, 70.7, 66.7, 65.3, 55.9, 55.8, 45.6, 45.2, 42.9, 40.4, 31.8, 31.8, 31.4, 28.9, 26.2, 23.4, 21.8, 19.7, 12.2.

Example 10

1(S),3(R)-Dihydroxy-20(R)-(3-((1-hydroxy-1-methyl)ethyl)phenylsulphonylmethyl)-9,10-seco-pregna-5(Z),7(E),10(19)-triene, Compound 158

Method: General Procedure 4.
Starting material V: Compound 71.
$^{13}$C NMR: δ=151.1, 147.6, 141.9, 140.1, 133.5, 129.8, 129.2, 126.3, 124.7, 123.9, 117.5, 111.8, 72.4, 70.8, 66.8, 61.8, 56.0, 55.9, 45.6, 45.2, 42.9, 40.5, 31.9, 30.6, 28.9, 26.4, 23.4, 21.7, 19.6, 12.4.

Example 11

1(S),3(R)-Dihydroxy-20(R)-(3-((1-hydroxy-1-methyl)ethyl)phenylsulphinylmethyl)-9,10-seco-pregna-5(Z),7(E),10(19)-triene, Compound 159 (isomer with Compound 157)

Method: General Procedure 4.
Starting material V: Compound 72.
$^{13}$C NMR: δ=150.8, 147.7, 144.9, 142.1, 133.4, 129.2, 127.2, 124.7, 122.2, 120.0, 117.5, 111.8, 72.5, 70.8, 66.8, 65.8, 56.4, 56.1, 45.8, 45.3, 42.9, 40.6, 31.9, 31.8, 31.1, 28.9, 27.0, 23.4, 22.0, 18.9, 12.5.

Example 12

1(S),3(R)-Dihydroxy-20(R)-(4-((1-hydroxy-1-methyl)ethyl)phenylsulphonylmethyl)-9,10-seco-pregna-5(Z),7(E),10(19)-triene, Compound 160

Method: General Procedure 4.
Starting material V: Compound 73.
$^{13}$C NMR: δ=155.4, 147.6, 141.8, 138.3, 133.6, 127.9, 125.5, 124.6, 117.6, 111.8, 72.4, 70.7, 66.8, 61.9, 56.1, 55.9, 45.6, 45.2, 42.8, 40.4, 31.8, 31.7, 30.5, 28.9, 26.4, 23.4, 21.7, 19.6, 12.3.

Example 13

1(S),3(R)-Dihydroxy-20(R)-(4-((1-hydroxy-1-methyl)ethyl)phenylsulphinylmethyl)-9,10-seco-pregna-5(Z),7(E),10(19)-triene Compound 161 (isomer with Compound 162)

Method: General Procedure 4.
Starting material V: Compound 75.
$^{13}$C NMR: δ=152.4, 147.7, 142.9, 142.1, 133.5, 125.6, 124.7, 123.9, 117.5, 111.8, 72.4, 70.8, 66.8, 65.8, 56.4, 56.1, 45.8, 45.2, 42.9, 40.6, 31.8, 31.1, 28.9, 27.0, 23.4, 22.0, 18.9, 12.5.

Example 14

1(S),3(R)-Dihydroxy-20(R)-(4-((1-hydroxy-1-methyl)ethyl)phenylsulphinylmethyl)-9,10-seco-pregna-5(Z),7(E),10(19)-triene, Compound 162 (isomer with Compound 161)

Method: General Procedure 4.
Starting material V: Compound 76.
$^{13}$C NMR: δ=153.3, 147.7, 141.8, 133.7, 125.5, 124.5, 117.5, 111.7, 72.2, 70.6, 66.7, 65.3, 55.9, 45.6, 45.2, 42.9, 40.3, 31.8, 31.4, 28.9, 26.1, 23.4, 21.8, 19.7, 12.2.

Example 15

1(S),3(R)-Dihydroxy-20(R)-(4-(hydroxymethyl)phenylthiomethyl)-9,10-seco-pregna-5(Z),7(E),10(19)-triene, Compound 163

Method: General procedure 2.
Compound II was replaced with Compound 89.
R—SH: 4-Mercaptobenzylalcohol.
The residue after work-up was purified by chromatography (silica gel; ethyl acetate as eluant) to give compound 163.

Example 16

1(S),3(R)-Dihydroxy-20(R)-(4-((1-hydroxy-1-ethyl)propyl))phenylthiomethyl)-9,10-seco-pregna-5(Z),7(E),10(19)-triene, Compound 164

Method: General procedure 2.
Compound II was replaced with Compound 89.
R—SH: 3-(4-Mercaptophenyl)pentan-3-ol.
The residue after work-up was purified by chromatography (silica gel; ethyl acetate as eluant) to give compound 164.

Example 17

1(S),3(R)-Dihydroxy-20(R)-(4-((1-hydroxy-1-methyl)ethyl))phenylthiomethyl)-22-methyl-9,10-seco-pregna-5(Z),7(E),10(19)-triene, Compound 165 (Isomer with compound 166)

Method: General procedure 2.
Compound II was replaced with Compound 94.
R—SH: 2-(4-Mercaptophenyl)propan-2-ol.
The residue after work-up was purified by chromatography (silica gel; ethyl acetate as eluant) to give compound 165.

Example 18

1(S),3(R)-Dihydroxy-20(R)-(4-((1-hydroxy-1-methyl)ethyl))phenylthiomethyl)-22-methyl-9,10-secopregna-5(Z),7(E),10(19)-triene, Compound 166 (Isomer with compound 165)

Method: General procedure 2.
Compound II was replaced with Compound 95.
R—SH: 2-(4-Mercaptophenyl)propan-2-ol.
The residue after work-up was purified by chromatography (silica gel; ethyl acetate as eluant) to give compound 166.

Example 19

Capsules Containing Compound 145

Compound 145 was dissolved in arachis oil to a final concentration of 10 µg/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 145 in oil solution, such that each capsule contained 1 µg of Compound 145.

Example 20

Drop Preparations Containing Compound 145

1) Drop Preparation Containing Compound 145 in the Form of an Oil Solution 0.1 g of Compound 145 and 0,5 g of D,L-alpha-tocopherole (as an antioxidant) are dissolved in Medium Chain Triglycerides (Ph.Eur) to obtain 100 L (=94.5 kg). The preparation is filtered, and the solution is transferred to brown bottles provided with a suitable dropper plug or drop-insert to enable dripping off of 1 ml of solution which is divided into 25 drops.

1 ml of solution contains 1 microgram of Compound 145 and 0.04 microgram of Compound 145 per drop. The bottle is closed with a suitable screw cap made of polypropylene.

2) Drop Preparation Containing Compound 145 in the Form of a Solubilised Aqueous Solution A) 0.2 g of Compound 145 and 2 g of D,L-alpha-tocopherole are dissolved in a stainless steel container in 10.2 kg (14 L) of ethanol 99.9%, and 2 kg of Cremophor RH40 (R) (Polyoxyl 40 hydrogenated castor oil).

B) 54 kg of Purified water, 0.015 kg of citric acid monohydrate, 0.950 kg of sodium citrate, 45 kg of Sorbitol, and 0.150 kg of methylparaben are dissolved at heating in a separate container.

Following cooling to below 25° C. solution B is slowly poured into solution A while stirring the mixture. Cremophor RH40 hereby forms a micellar solution wherein the water insoluble Compound 145 and D,L-alpha-tocopherole remains in solution in the preparation. Finally, purified water is added to the preparation to obtain 113 kg (=100 L) of preparation of a pH in the range (6.5–7.5). The preparation is filtered and bottled in brown bottles provided with a suitable dropper plug or drop insert and a matching screw cap.

1 ml of the preparation contains 2 microgram of Compound 145 to be divided into, e.g., 20 drops each corresponding to 0.1 microgram of Compound 145.

Example 21

Injection Fluid Containing Compound 145

| | |
|---|---|
| Compound 145 (active substance) | 10 µg |
| Disodium phosphate dihydrate (buffer) | 15.4 mg |
| Sodium dihydrogen phosphate dihydrate (buffer) | 2 mg |
| Sodium chloride | 0.8 mg |
| Sodium ascorbate (antioxidant) | 5 mg |
| Solutol ® HS 15 from BASF (solubilizer) | 5 mg |
| Water for injection | ad 1 ml |

Solutol® HS 15 is dissolved in the water for injection by heating it to a temperature of at the most 80° C. A cover of nitrogen is applied. The buffer substances and the sodium chloride are added and then the solution is cooled to at the most 30° C. Then sodium ascorbate is added and, finally, compound 145 is dissolved in the solution obtained.

The solution is subjected to sterile filtration and is autoclaved at an appropriate time-temperature condition.

The invention claimed is:

1. A method for the treatment of osteoporosis comprising administering to a patient in need thereof an effective amount of a compound of the formula I

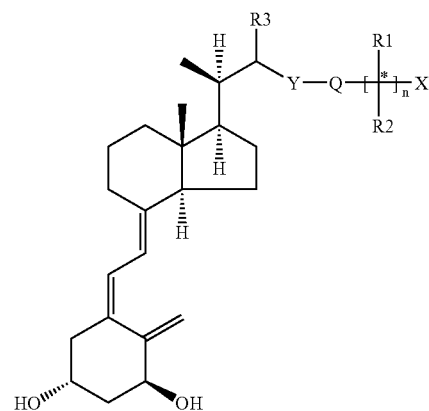

wherein
X represents hydrogen or hydroxy;
Y represents oxygen or sulphur or oxidized sulphur selected from the groups S(O) and S(O$_2$);
$R^1$ and $R^2$, which may be the same or different, represent hydrogen or a residue after removal of 1 hydrogen atom from a straight, branched or cyclic, saturated or unsaturated, $C_1$–$C_6$-hydrocarbon; or $R^1$ and $R^2$, together with the carbon atom to which they are attached (marked with an asterisk in formula I), bearing the group X, form a $C_3$–$C_8$ carbocyclic ring;
Q represents a diradi-cal residue after removal of 2 hydrogen atoms from a straight, branched or cyclic, saturated or unsaturated $C_1$–$C_8$-hydrocarbon;
$R^3$ represents hydrogen or a residue after removal of 1 hydrogen atom from a straight, branched or cyclic, saturated or unsaturated $C_1$–$C_6$-hydrocarbon;
$R^1$, $R^2$ and/or Q is optionally substituted with one or more deuterium or fluorine atoms; and
n is 0 or 1;

and derivatives of the compounds of formula I in which one or more hydroxy groups have been transformed into —O-acyl or —O-glycosyl groups, or a phosphate ester, such masked groups being hydrolyzable in vivo; or administering to a patient in need thereof an effective amount of a compound of formula Ia

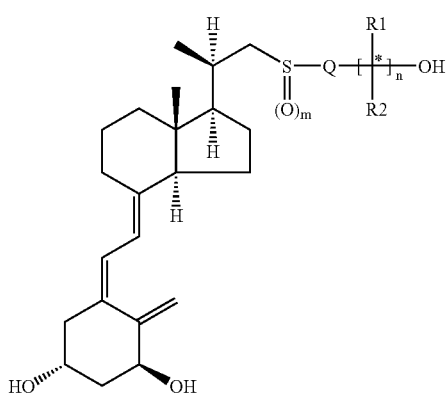

wherein $R^1$, $R^2$, and Q have the meanings specified above; m=0, 1 or 2; and n=1.

2. The method according to claim 1, wherein Y represents sulphur or oxidized sulphur selected from the groups S(O) or S(O$_2$).

3. The method according to claim 1, wherein $R^1$ and $R^2$, together with the carbon atom to which they are attached (marked with an asterisk in formula I), bearing the group X, form a $C_3$–$C_5$ alkylene group or a $C_3$–$C_5$ carbocyclic ring.

4. The method according to claim 1, wherein Q represents a phenylene group optionally substituted with one or more fluorine atoms.

5. The method according to claim 1, wherein $R^3$ represents hydrogen.

6. The method according to claim 1, wherein n is 1.

7. The method according to claim 1, wherein the compound is selected from the group consisting of:
  1(S),3(R)-Dihydroxy-20(R)-(3-hydroxy-3-methyl-1-butoxymethyl)-9,10-seco-pregna-5(Z),7(E),10(19)-triene (Compound 102),
  1(S),3(R)-Dihydroxy-20(R)-(3-hydroxy-3-ethyl-1-pentyloxymethyl-9,10-seco-pregna-5(Z),7(E),10(19)-triene (Compound 103),
  1(S),3(R)-Dihydroxy-20(R)-(4-hydroxy-4-methyl-1-pentyloxymethyl)-9,10-seco-pregna-(Z),7(E),10(19)-triene (Compound 106),
  1(S),3(R)-Dihydroxy-20(R)-(4-hydroxy-4-methyl-1-pent-2(E)-enyloxymethyl-9,10-seco-pregna-5(Z),7(E),10(19)-triene (Compound 107)
  1(S),3(R)-Dihydroxy-20(R)-(4-hydroxy-4-methyl-1-pent-2-ynyloxymethyl)-9,10-seco-pregna-5(Z),7(E),10(19)-triene (Compound 108),
  1(S),3(R)-Dihydroxy-20(R)-(4-hydroxy-4-trifluoromethyl-5,5,5-trifluoro-1-pent-2-ynyloxymetyl)-9,10-seco-pregna-5(Z),7(E),10(19)-triene (Compound 109),
  1(S),3(R)-Dihydroxy-20(R)-[3-(2-hydroxy-2-propyl)-phenoxymethyl]-9,10-seco-pregna-5(Z),7(E),10(19)-triene (Compound 111),
  1(S),3(R)-Dihydroxy-20(R)-(2-hydroxy-2-methyl-1-propylthiomethyl)-9,10-seco-pregna-5(Z),7(E),10(19)-triene (Compound 116),
  1(S),3(R)-Dihydroxy-20(R)-(3-hydroxy-3-methyl-1-butylthiomethyl)-9,10-seco-pregna-5(Z),7(E),10(19)-triene (Compound 117),
  1(S),3(R)-Dihydroxy-20(R)-(3-hydroxy-3-ethyl-1-pentylthiomethyl)-9,10-seco-pregna-5(Z),7(E),10(19)-triene (Compound 121),
  1(S),3(R)-Dihydroxy-20(R)-(5-hydroxy-5-methyl-1-hexyloxymethyl)-9,10-seco-pregna-5(Z),7(E),10(19)-triene (Compound 126),
  1(S),3(R)-Dihydroxy-20(R)-[2-(2-hydroxy-2-propyl)-phenoxymethyl]-9,10-seco-pregna-5(Z),7(E),10(19)-triene (Compound 127),
  1(S),3(R)-Dihydroxy-20(R)-[2-(3-hydroxy-3-pentyl)-phenoxymethyl]-9,10-seco-pregna-5(Z),7(E),10(19)-triene (Compound 128),
  1(S),3(R)-Dihydroxy-20(R)-[3-(3-hydroxy-3-pentyl)-phenoxymethyl]-9,10-seco-pregna-5(Z),7(E),10(19)-triene (Compound 129),
  1(S),3(R)-Dihydroxy-20(R)-[4-(2-hydroxy-2-propyl)-phenoxymethyl]-9,10-seco-pregna-5(Z),7(E),10(19)-triene (Compound 130),
  1(S),3(R)-Dihydroxy-20(R)-[4-(3-hydroxy-3-pentyl)-phenoxymethyl]-9,10-seco-pregna-5(Z),7(E),10(19)-triene (Compound 131),
  1(S),3(R)-Dihydroxy-20(R)-[3-(hydroxymethyl)-phenoxymethyl]-9,10-seco-pregna-5(Z),7(E),10(19)-triene (Compound 132),
  1(S),3(R)-Dihydroxy-20(R)-(3-hydroxy-3-ethyl-1-pentylsulphinylmethyl-9,10-seco-pregna-5(Z),7(E),10 (19)-triene (Compound 133),
  1(S),3(R)-Dihydroxy-20(R)-(3-hydroxy-3-ethyl-1-pentylsulphinylmethyl)-9,10-seco-pregna-5(Z),7(E),10 (19)-triene (Compound 134),
  1(S),3(R)-Dihydroxy-20(R)-(3-hydroxy-3-ethyl-1-pentylsulphonylmethyl)-9,10-seco-pregna-5(Z),7(E),-10 (19)-triene (Compound 135),
  1(S),3(R)-Dihydroxy-20(R)-(4-hydroxy-4-methyl-1-pentylthiomethyl)-9,10-seco-pregna-5(Z),7(E),10(19)-triene (Compound 136),
  1(S),3(R)-Dihydroxy-20(R)-(3-(hydroxymethyl)phenylthiomethyl)-9,10-seco-pregna-5(Z),7(E),10(19)-triene (Compound 137),
  1(S),3(R)-Dihydroxy-20(R)-(3-((1-hydroxy-1-methyl)ethyl)phenylthiomethyl)-9,10-seco-pregna-5(Z),7(E),-10(19)-triene (Compound 138),
  (S),3(R)-Dihydroxy-20(R)-(4-hydroxy-4-ethyl-1-hex-2-ynyloxymethyl)-9,10-seco-pregna-5(Z),7(E),10(19)-triene (Compound 139),
  1(S),3(R)-Dihydroxy-20(R)-(2-hydroxyphenoxymethyl)-9,10-seco-pregna-5(Z),7(E),10(19)-triene Compound 140),
  1(S),3(R)-Dihydroxy-20(R)-(3-hydroxyphenoxymethyl)-9,10-seco-pregna-5(Z),7(E),10(19)-triene (Compound 141),
  1(S),3(R)-Dihydroxy-20(R)-(2-((1-hydroxy-1-methyl)ethyl)phenylthiomethyl)-9,10-seco-pregna-5(Z),7(E),10(19)-triene (Compound 142),
  1(S),3(R)-Dihydroxy-20(R)-(3-((1-hydroxy-1-ethyl)propyl)phenylthiomethyl)-9,10-seco-pregna-5(Z),7(E),10 (19)-triene (Compound 144),
  1(S),3(R)-Dihydroxy-20(R)-(4-((1-hydroxy-1-methyl)ethyl)phenylthiomethyl)-9,10-seco-pregna-5(Z),7(E),10(19)-triene (Compound 145),
  1(S),3(R)-Dihydroxy-20(R)-(2-hydroxy)phenylthiomethyl)-9,10-seco-pregna-5(Z),7(E),10(19)-triene (Compound 147), 1(S),3(R)-Dihydroxy-20(R)-(3,3-difluoro-4-hydroxy-4-methyl-1-pentyloxymethyl)-9,10-seco-pregna-5(Z),-7(E),10(19)-triene (Compound 153), 1(S),3(R)-Dihydroxy-20(R)-(4-(hydroxymethyl)phenylthiomethyl)-9,10-seco-pregna-5(Z),7(E),10(19)-triene, (Compound 163), 1(S),3(R)-Dihydroxy-20(R)-(4-((1-hydroxy-1 ethyl)propyl))phenylthiomethyl)-9,10-seco-pregna-5(Z),7(E),10(19)-triene, (Compound 164), 1(S),3(R)-Dihydroxy-20(R)-(4-((1-hydroxy-1-methyl)ethyl))phenylthiomethyl)-22(R)-methyl-9,10-seco-pregna-5(Z),7(E),10(19)-triene, (Compound 165), and 1(S),3(R)-Dihydroxy-20(R)-(4-((1-hydroxy-1-methyl)ethyl))phenylthiomethyl)-22(S)-methyl-9,10-seco-pregna-5(Z),7(E),10(19)-triene, (Compound 166).

8. The method according to claim 1, wherein a compound according to formula Ia is administered and wherein Q represents an unsubstituted phenylene group.

9. The method according to claim 1, wherein a compound of formula Ia is administered and is selected from the group consisting of:

1(S),3(R)-Dihydroxy-20(R)-(4-hydroxy-phenylthiomethyl)-9,10-seco-pregna-5(Z),7(E),10(19)-triene (Compound 149), 1(S),3(R)-Dihydroxy-20(R)-(3,3-difluoro-4-hydroxy-4-methyl-1-pentylthiomethyl)-9,10-seco-pregna-5(Z),7(E),10(19)-triene (Compound 155), 1(S),3(R)-Dihydroxy-20(R)-(3,3-difluoro-4-hydroxy-4-methyl-1-pentylsulphinylmethyl)-9,10-seco-pregna-5(Z),7(E),10(19)-triene (Compound 156), 1(S),3(R)-Dihydroxy-20(R)-(3-((1-hydroxy-1-methyl)ethyl)phenylsulphinylmethyl)-9,10-seco-pregna-5(Z),7(E),10(19)-triene (Compound 157)(diastereoisomeric sulfoxide of compound 159), 1(S),3(R)-Dihydroxy-20(R)-(3-((1-hydroxy-1-methyl)ethyl)phenylsulphonylmethyl)-9,10-seco-pregna-5(Z),7(E),10(19)-triene (Compound 158), 1(S),3(R)-Dihydroxy-20(R)-(3-((1-hydroxy-1-methyl)ethyl)phenylsulphinylmethyl)-9,10-seco-pregna-5(Z),7(E),10(19)-triene (Compound 159)(diastereoisomeric sulfoxide of compound 157), 1(S),3(R)-Dihydroxy-20(R)-(4-((1-hydroxy-1-methyl)ethyl)phenylsulphonylmethyl)-9,10-seco-pregna-5(Z),7(E),10(19)-triene (Compound 160), 1(S),3(R)-Dihydroxy-20(R)-(4-((1-hydroxy-1-methyl)ethyl)phenylsulphinylmethyl)-9,10-seco-pregna-S(Z),7(E),10(19)-triene (Compound 161)(diastereoisomeric sulfoxide of compound 162) and 1(S),3(R)-Dihydroxy-20(R)-(4-((1-hydroxy-1-methyl)ethyl)phenylsulphinylmethyl)-9,10-seco-pregna-5(Z),7(E),10(19)-triene (Compound 162)(diastereoisomeric sulfoxide of compound 161.

10. The method according to claim 1, wherein the compound is administered together with pharmaceutically acceptable, non-toxic carriers and/or auxiliary agents.

11. The method according to claim 10, wherein the compound is in dosage unit form.

12. The method according to claim 11, wherein the dosage unit form contains from about 0.5 µg–about 6 mg of a compound of formula I or Ia.

13. A method for the treatment of osteoporosis comprising administering to a patient in need thereof an effective amount of a compound of the formula Ia

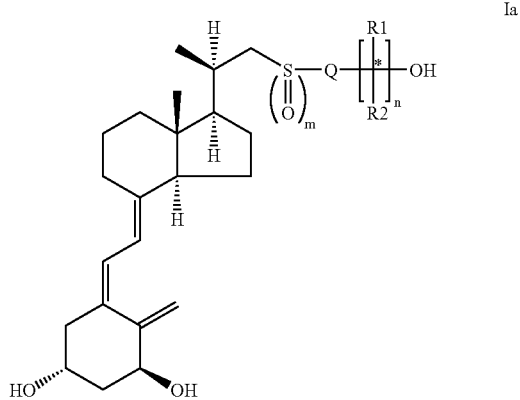

Ia wherein $R^1$ and $R^2$, which may be the same or different, represent hydrogen or a residue after removal of 1 hydrogen atom from a straight, branched or cyclic, saturated or unsaturated, $C_1$–$C_6$-hydrocarbon; or $R^1$ and $R^2$, together with the carbon atom to which they are attached (marked with an asterisk in formula Ia), bearing the group X, form a $C_3$–$C_8$ carbocyclic ring;

Q represents a diradical residue after removal of 2 hydrogen atoms from a straight, branched or cyclic, saturated or unsaturated $C_1$–$C_8$-hydrocarbon;

$R^1$, $R^2$ and/or Q is optionally substituted with one or more deuterium or fluorine atoms;

m=0, 1 or 2; and n=1.

14. A method for the treatment of osteoporosis comprising administering to a patient in need thereof an effective amount of a compound of formula I

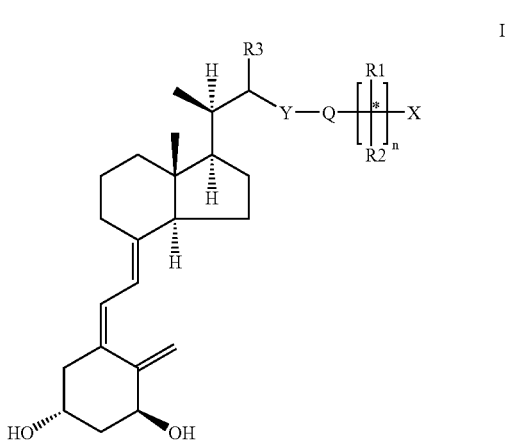

I wherein

X represents hydrogen or hydroxy;

Y represents oxygen or sulphur or oxidized sulphur selected from the groups S(O) and S(O$_2$);

$R^1$ and $R^2$, which may be the same or different, represent hydrogen or a residue after removal of 1 hydrogen atom from a straight, branched or cyclic, saturated or unsaturated, $C_1$–$C_6$-hydrocarbon; or $R^1$ and $R^2$, together with the carbon atom to which they are attached (marked with an asterisk in formula I), bearing the group X, form a $C_3$–$C_8$ carbocyclic ring;

Q represents a diradical residue after removal of 2 hydrogen atoms from a straight, branched or cyclic, saturated or unsaturated $C_1$–$C_8$-hydrocarbon;

$R^3$ represents hydrogen or a residue after removal of 1 hydrogen atom from a straight, branched or cyclic, saturated or unsaturated $C_1$–$C_6$-hydrocarbon;

$R^1$, $R^2$ and/or Q is optionally substituted with one or more deuterium or fluorine atoms; and n is 0 or 1;

and derivatives of the compounds of formula I in which one or more hydroxy groups have been transformed into —O-acyl or —O-glycosyl groups, or a phosphate ester, such masked groups being hydrolyzable in vivo.

15. The method according to claim 11, wherein the dosage unit form contains from about 0.5 μg–about 6 mg of a compound of formula I or Ia.

16. The method according to claim 3, wherein said $C_3$–$C_5$ carboxylic ring is saturated.

17. The method according to claim 1, wherein the method is directed to the treatment of steroid induced, senile or postmenopausal osteoporosis.

18. The method according to claim 13, wherein the method is directed to the treatment of steroid induced, senile or postmenopausal osteoporosis.

19. The method according to claim 14, wherein the method is directed to the treatment of steroid induced, senile or postmenopausal osteoporosis.

* * * * *